United States Patent
Damon et al.

(10) Patent No.: US 9,198,740 B2
(45) Date of Patent: Dec. 1, 2015

(54) ORTHODONTIC BRACKET

(71) Applicants: Paul L. Damon, Spokane, WA (US); Dwight H. Damon, Spokane, WA (US)

(72) Inventors: Paul L. Damon, Spokane, WA (US); Dwight H. Damon, Spokane, WA (US)

(73) Assignee: PREMIER ORTHODONTIC DESIGNS, LLLP, Carson City, NV (US)

( * ) Notice: Subject to any disclaimer, the term of this patent is extended or adjusted under 35 U.S.C. 154(b) by 58 days.

(21) Appl. No.: 13/970,100

(22) Filed: Aug. 19, 2013

(65) Prior Publication Data

US 2015/0050612 A1 Feb. 19, 2015

(51) Int. Cl.
| A61C 3/00 | (2006.01) |
| A61C 7/14 | (2006.01) |
| A61C 7/28 | (2006.01) |
| A61C 7/30 | (2006.01) |

(52) U.S. Cl.
CPC . *A61C 7/141* (2013.01); *A61C 7/14* (2013.01); *A61C 7/287* (2013.01); *A61C 7/30* (2013.01)

(58) Field of Classification Search
CPC .............. A61C 7/12; A61C 7/14; A61C 7/16; A61C 7/28; A61C 7/141; A61C 7/146; A61C 7/285
USPC ...................................... 433/8–24
See application file for complete search history.

(56) References Cited

U.S. PATENT DOCUMENTS

| 3,721,005 | A | * | 3/1973 | Cohen ............................. 433/16 |
| 4,243,387 | A | * | 1/1981 | Prins ............................... 433/16 |
| 4,249,897 | A |   | 2/1981 | Anderson |
| 4,496,317 | A | * | 1/1985 | Hulsey ............................. 433/10 |
| 4,850,865 | A | * | 7/1989 | Napolitano ....................... 433/8 |
| 5,302,121 | A |   | 4/1994 | Gagin |
| 5,358,402 | A | * | 10/1994 | Reed et al. ....................... 433/8 |
| 5,380,196 | A | * | 1/1995 | Kelly et al. ...................... 433/8 |
| 5,618,175 | A | * | 4/1997 | Reher et al. ..................... 433/8 |
| 5,954,502 | A |   | 9/1999 | Tuenge et al. |
| 6,264,469 | B1 | * | 7/2001 | Moschik .......................... 433/8 |
| 6,305,932 | B1 | * | 10/2001 | Mottate ............................ 433/8 |
| 7,192,274 | B2 | * | 3/2007 | Stadtmiller et al. .............. 433/8 |
| 7,431,586 | B1 |   | 10/2008 | Silverman |
| 8,550,814 | B1 | * | 10/2013 | Collins ............................ 433/9 |
| 2002/0110771 | A1 |   | 8/2002 | Abels et al. |
| 2005/0239012 | A1 | * | 10/2005 | Bathen et al. ................... 433/10 |
| 2006/0051721 | A1 | * | 3/2006 | Carriere Lluch ............... 433/10 |

(Continued)

FOREIGN PATENT DOCUMENTS

| WO | WO 9509580 A1 * | 4/1995 | ............... A61C 7/12 |
| WO | WO 2011141937 A1 * | 11/2011 |

OTHER PUBLICATIONS

PCT Search Report dated Apr. 14, 2014.

(Continued)

*Primary Examiner* — Cris L Rodriguez
*Assistant Examiner* — Matthew Saunders
(74) *Attorney, Agent, or Firm* — Randall Danskin P.S.

(57) ABSTRACT

An orthodontic bracket is described, and which includes a bracket base, which is releasably affixed to a patient's tooth; a bracket body borne on the bracket base, and which defines an arch wire slot, and which further has a selectively adjustable cross-sectional dimension; and an arch wire is received within the arch wire slot, and where the described embodiment of the bracket body, acting in combination with the arch wire is adjustable so as to provide a multiplicity of selective torque expressions, which act upon a patient's tooth.

6 Claims, 24 Drawing Sheets

(56) References Cited

U.S. PATENT DOCUMENTS

| | | | |
|---|---|---|---|
| 2008/0293005 A1* | 11/2008 | Rahlis et al. | 433/16 |
| 2009/0004619 A1* | 1/2009 | Oda et al. | 433/24 |
| 2011/0183280 A1* | 7/2011 | Cosse et al. | 433/13 |
| 2011/0311934 A1 | 12/2011 | Kantomaa | |
| 2012/0064475 A1 | 3/2012 | Lewis et al. | |
| 2012/0122050 A1 | 5/2012 | Bathen et al. | |
| 2012/0308952 A1* | 12/2012 | Cosse | 433/3 |
| 2014/0272751 A1* | 9/2014 | Cosse et al. | 433/9 |

OTHER PUBLICATIONS

PCT Report dated Mar. 10, 2015.
U.S. Appl. No. 13/745,638, filed Jan. 18, 2013, Entitled Orthodontic Bracket by Paul L. Damon et al.

* cited by examiner

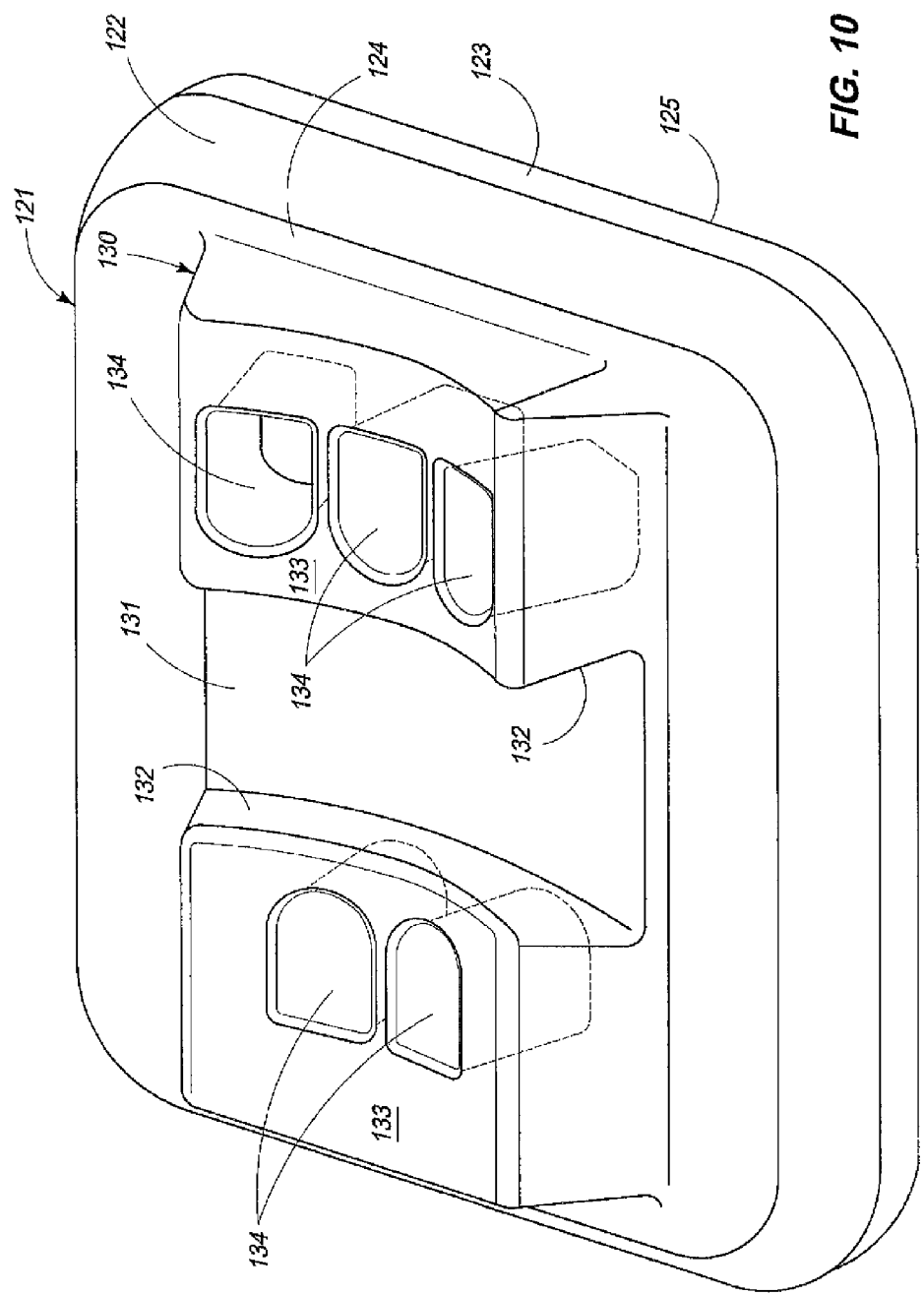

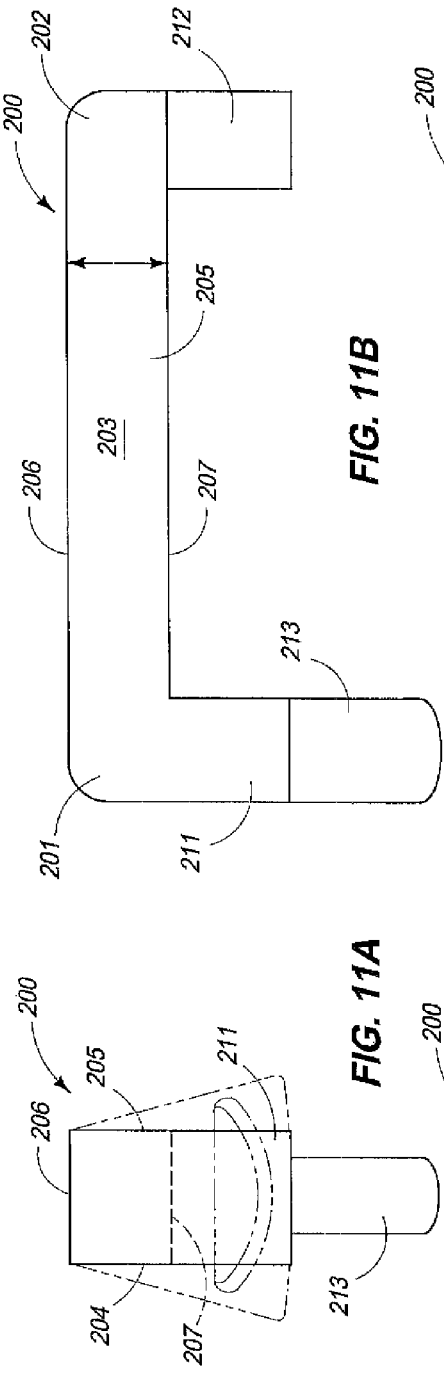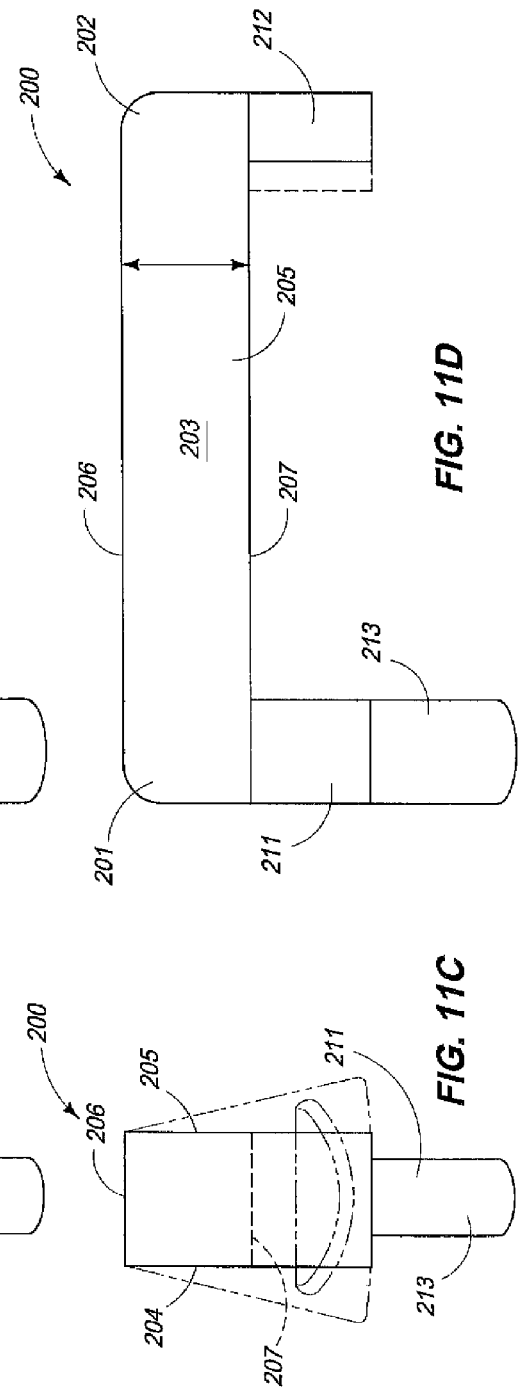

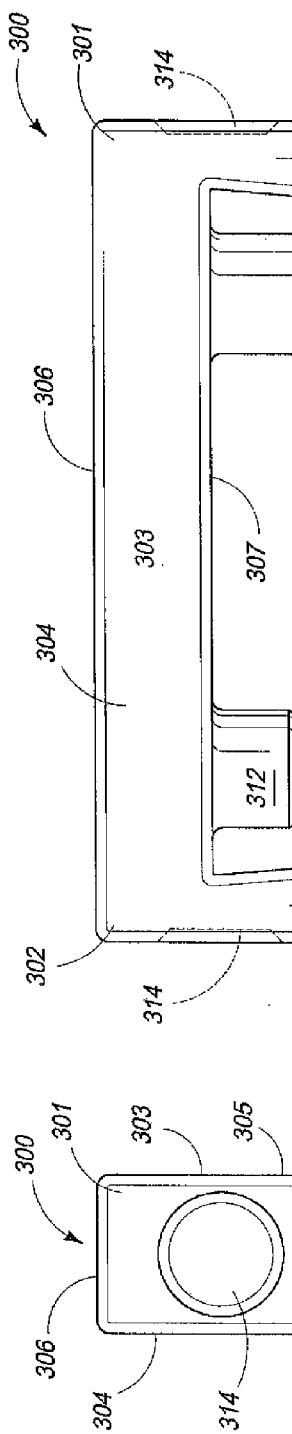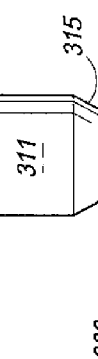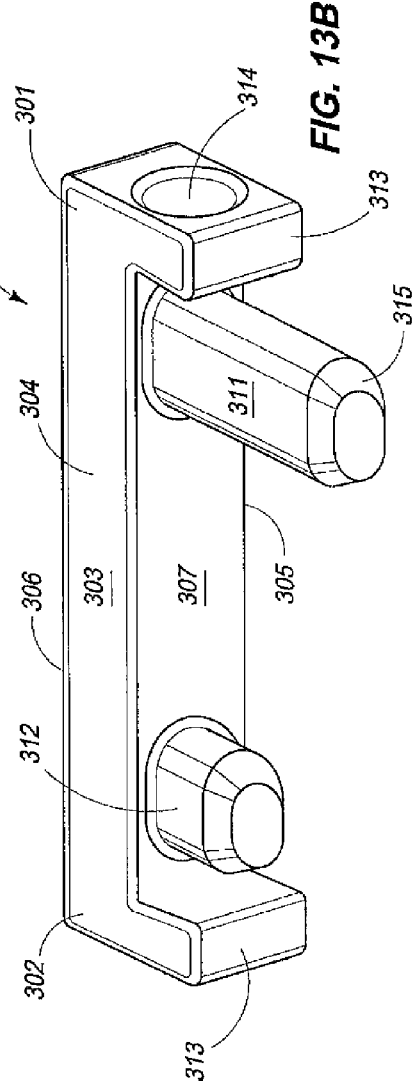

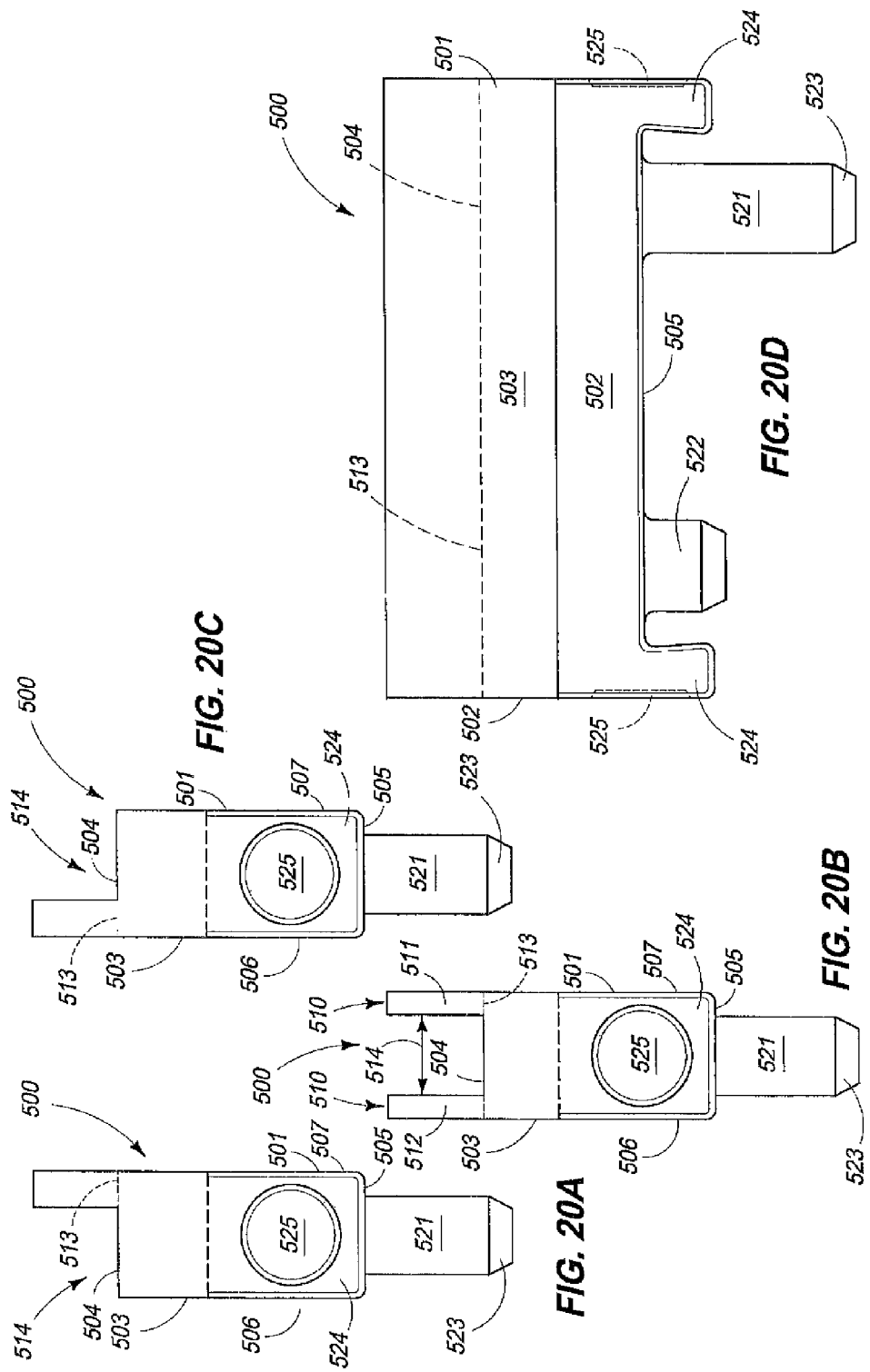

ORTHODONTIC BRACKET

TECHNICAL FIELD

The present invention relates to an orthodontic bracket, and more specifically to an orthodontic bracket which defines a transversely disposed arch wire slot which is selectively adjustable so as to provide a variable cross-sectional dimension, and which further provides a multiplicity of selective torque expressions which individually forcibly act upon a patient's tooth.

BACKGROUND OF THE INVENTION

In our earlier U.S. patent application Ser. No. 13/745,638, and which was filed on Jan. 18, 2013, we described an orthodontic bracket which when used in combination with an arch wire provides first, second, and third orders of movement of the patient's tooth without a clinically predetermined manipulation of the arch wire which is received in the transversely disposed arch wire slot. The various forms of the invention as disclosed in this pending US patent application provides a multitude of patient and clinical advantages not possible in orthodontic appliances which have been utilized heretofore. The teachings of this prior co-pending patent application are incorporated by reference herein.

Generally speaking, first order movements are commonly thought of as tooth rotation, and in/out tooth control. Further, second order movements are often referred to as "tipping" the root in a mesial and/or distal angulation or elevation, and/or depression of a tooth position. Further, third order movement, or "couples," have resulted in the expression of "torque" which causes the axial inclination of a tooth from a flared or uprighted orientation to its final and desired position.

From its earliest utilization, and to achieve ideal tooth positioning, a clinician has, heretofore, been required to bend round and rectangular shaped arch wires to express the in/out, up/down, tipping, and torque to accomplish a final, desired tooth position. This activity not only took long periods of time, and advanced clinical practice skills, but it was nearly impossible for most clinicians to control the resulting treatment forces applied in all planes of space. As a result, treatment times for patients were often unduly long in duration, and the resulting treatment forces which were applied often had a negative long term impact on the patient's bone and tissue.

In 1970, Dr. Larry Andrews invented what was later termed a "straight wire" appliance. This bracket design allowed significant improvements to first and second order movements, and lessened the need for the predetermined bending of the arch wires. However, this design still lacked adequate third order control of tooth axial inclination. The term "straight wire orthodontics" misled many clinicians to believe that only one bracket torque prescription on each anterior tooth was adequate to express a final desired tooth position. Unfortunately, without bending rectangular arch wires to individualize finishing torque on individual teeth, this had nearly the same effect as treating patients using only round wires in the bracket arch wire slot. This, of course, negated any third order control. For example, if a 0.019 inch×0.025 inch stainless steel rectangular working or finishing arch wire is placed in a 0.022 inch arch wire slot, there is approximately 11 to 12 degrees of play, or freedom of movement, in either direction, for a total of 22 to 24 degrees of play or movement before a third order "torquing couple" is achieved between two opposite corners of the rectangular shaped arch wire, and the opposing walls of the bracket arch wire slot. Over the years, some clinicians have tried to fill the arch wire slot with larger cross-sectional rectangular arch wires to achieve third order control, but many have found it difficult to finally position teeth due to the binding, and friction which is experienced in the arch wire-bracket interface. The use of these larger dimensioned finishing rectangular arch wires in most clinical settings resulted in the application of unfavorable physical forces, in both magnitude, and direction which made final tooth positioning far more challenging for the clinician. This also resulted in potentially negative, long term impact on the patient's bone and tissue. For this reason, most clinicians have tried to bend the appropriate amount of torquing couple into the smaller dimensioned rectangular arch wires so as to correctly procline or upright the axial inclination of the teeth to their final desired position. It should be readily apparent that the multitude of variations which may impact the third order tooth movements are many, and consequently, orthodontists typically are not readily able, in most clinical settings, to rapidly, and accurately calculate the amount of third order couple that is needed, and the appropriate amount of force that should be applied to a given tooth to achieve the desired amount of tooth movement. Consequently, because of clinician miscalculation, treatment times for any given patient are often extended as individual clinician's strive to achieve the desired tooth position, and alignment which is appropriate. Additionally, it will be recognized that this miscalculation of the appropriate amount of force to express third order torque may result in excessive discomfort to the patient, and as previously mentioned, potentially negative long term potential health issues may arise for the orthodontically treated patient.

While the numerous advantages to be achieved by utilizing the various forms of the orthodontic bracket as seen in our earlier filed application Ser. No. 13/745,638 are many, an ongoing need remains for the development of an orthodontic bracket which is readily and easily utilized by the clinician, in a clinical setting, and which further provides a rapid means for adjusting the orthodontic bracket in order to achieve assorted first, second and third order movements of a patient's tooth in a manner not possible heretofore. A new orthodontic bracket which achieves these objectives is the subject matter of the present application.

SUMMARY OF THE INVENTION

A first aspect of the present invention relates to an orthodontic bracket which includes a bracket base which is releasably affixed to an anterior facing surface of a patient's tooth; a bracket body borne on the bracket base, and which has anterior facing surface with defines a transversely disposed arch wire slot, and which further has opposite first and second ends, and wherein the arch wire slot has a selectively adjustable cross-sectional dimension, and an arch wire received within the transversely disposed, arch wire slot, and wherein the bracket body, acting in combination with the arch wire, is adjustable so as to provide a multiplicity of selective torque expressions which individually, forcibly act upon the patient's tooth.

Another aspect of the present invention relates to an orthodontic bracket which includes a bracket base which is releasably affixed to an anterior facing surface of a patient's tooth; a bracket body which moveably cooperates with the bracket base, and wherein the bracket body has an anterior facing surface which defines, at least in part, a transversely disposed arch wire slot which communicates with the anterior facing surface of the bracket body; a bracket body insert which is releasably received within the transversely disposed arch wire slot, and which further forms, at least in part, a portion of the transversely disposed arch wire slot, and wherein the bracket body insert further selectively fixes the orientation of the moveable bracket body relative to the bracket base; and an arch wire received within the transversely disposed arch wire slot, and wherein the moveable bracket body, acting in combination with the bracket body insert, each respectively engage the arch wire to provide a multiplicity of torque expressions which individually forcibly act upon the patient's tooth.

Still another aspect of the present invention relates to an orthodontic bracket which includes a bracket base which is releasably affixed to an anterior facing surface of a patient's tooth; a bracket body mounted on the bracket base, and which has an anterior facing surface which defines a transversely disposed cavity; an arch wire insert having a main body which is defined by a longitudinal axis, and which is further received within the transversely disposed cavity, and wherein the main body of the arch wire insert further defines, at least in part, a transversely disposed arch wire slot having a selectively adjustable cross-sectional dimension, and wherein the arch wire insert is selectively rotatable about the longitudinal axis thereof; a bracket body insert which is releasably received within the transversely disposed arch wire slot, and which further has a main body which forms, at least in part, a portion of the arch wire slot, and wherein the bracket body insert substantially releasably fixes the rotatable orientation of the arch wire insert relative to the bracket body, and further selectively adjusts the cross-sectional dimension of the transversely disposed arch wire slot while the bracket base is releasably attached to the anterior facing surface of the patient's tooth; and an arch wire received within the transversely disposed arch wire slot, and which, acting in combination with the arch wire insert, provides a multiplicity of selective torque expressions which individually forcibly act upon the patient's tooth.

Moreover, another aspect of the present invention relates to an orthodontic bracket which includes a bracket base having a pad which is releasably affixed to an anterior facing surface of a patient's tooth, and wherein the bracket base has an anterior facing surface which defines a coupling portion having a curved anterior facing surface, and wherein a multiplicity of engagement regions are formed in a predetermined spatial pattern in the curved anterior facing surface of the coupling portion; a bracket body which matingly, and moveably cooperates with the bracket base, and which has an anterior facing surface defining an aperture, and which further defines, in part, an arch wire slot having spaced, top and bottom surfaces, and a given cross-sectional dimension, and wherein the transversely disposed arch wire slot communicates with the aperture which is defined by the anterior facing surface of the bracket body, and is further accessible from the anterior facing surface of the bracket body, and wherein the bracket body has a complementary, curved, posterior facing surface which matingly, and moveably engages the curved, anterior facing surface of the coupling portion of the bracket base; a bracket body insert which is releasably received within the transversely disposed arch wire slot, and which further has a main body which forms a back wall of the transversely disposed arch wire slot, and wherein the back wall extends between the top and bottom surfaces of the arch wire slot, and wherein the bracket body insert further has a main body with a predetermined length, height and thickness dimension, and wherein the bracket body insert selectively adjusts the cross-sectional dimension of the transversely disposed arch wire slot, and wherein the bracket body insert further includes an engagement member which is oriented substantially perpendicularly relative to the main body thereof, and which further has a distal end which is operable to be received in one of the engagement regions formed in the bracket base, and wherein the engagement member of the bracket body insert is effective in selectively fixing the rotatable orientation of the moveable bracket body relative to the bracket base; and an arch wire received within the transversely disposed arch wire slot, and wherein the moveable bracket body, acting in combination with the bracket body insert, selectively provides first, second, and third order torque couples to a patient's tooth to achieve a clinically desired positional correction of the patient's tooth without the replacement of the bracket base during a predetermined clinical treatment regimen.

These and other aspects of the present invention will be described in greater detail hereinafter.

BRIEF DESCRIPTION OF THE DRAWINGS

Preferred embodiments of the invention are described below with reference to the following accompanying drawings.

FIG. 1A is a greatly simplified view of a patient's tooth showing individual orders of movement.

FIG. 10 is a perspective, greatly enlarged, top plan view of a bracket base which finds usefulness in the second form of the orthodontic bracket of the present invention.

FIG. 11A is an end view of a bracket body insert which finds usefulness in the second form of the orthodontic bracket of the present invention.

FIG. 11B is a side elevation view of one possible form of the bracket body insert which finds usefulness in the second form of the orthodontic bracket of the present invention.

FIG. 11C is an end view of yet another form of a bracket body insert which finds usefulness in the second form of the orthodontic bracket of the present invention.

FIG. 11D is a side elevation view of still another form of the bracket body insert which finds usefulness in the second form of the orthodontic bracket as previously shown.

FIG. 13A shows a side elevation view of a bracket body insert which finds usefulness when employed with the third form of the present invention.

FIG. 13B shows a perspective, side elevation view of a bracket body insert which finds usefulness when employed with the third form of the invention.

FIG. 13C shows and end view of a bracket body insert which finds usefulness when employed with the third form of the present invention.

FIG. 20A shows an end view of a bracket body insert which finds usefulness in the various forms of the invention.

FIG. 20B shows an end view of an alternative form of a bracket body insert which finds usefulness in the various forms of the invention.

FIG. 20C shows an end view of another alternative form of a bracket body insert, and which finds usefulness in the various forms of the invention.

FIG. 20D shows a side elevation view of the bracket body insert as illustrated in FIGS. 20A, and 20C, respectively.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
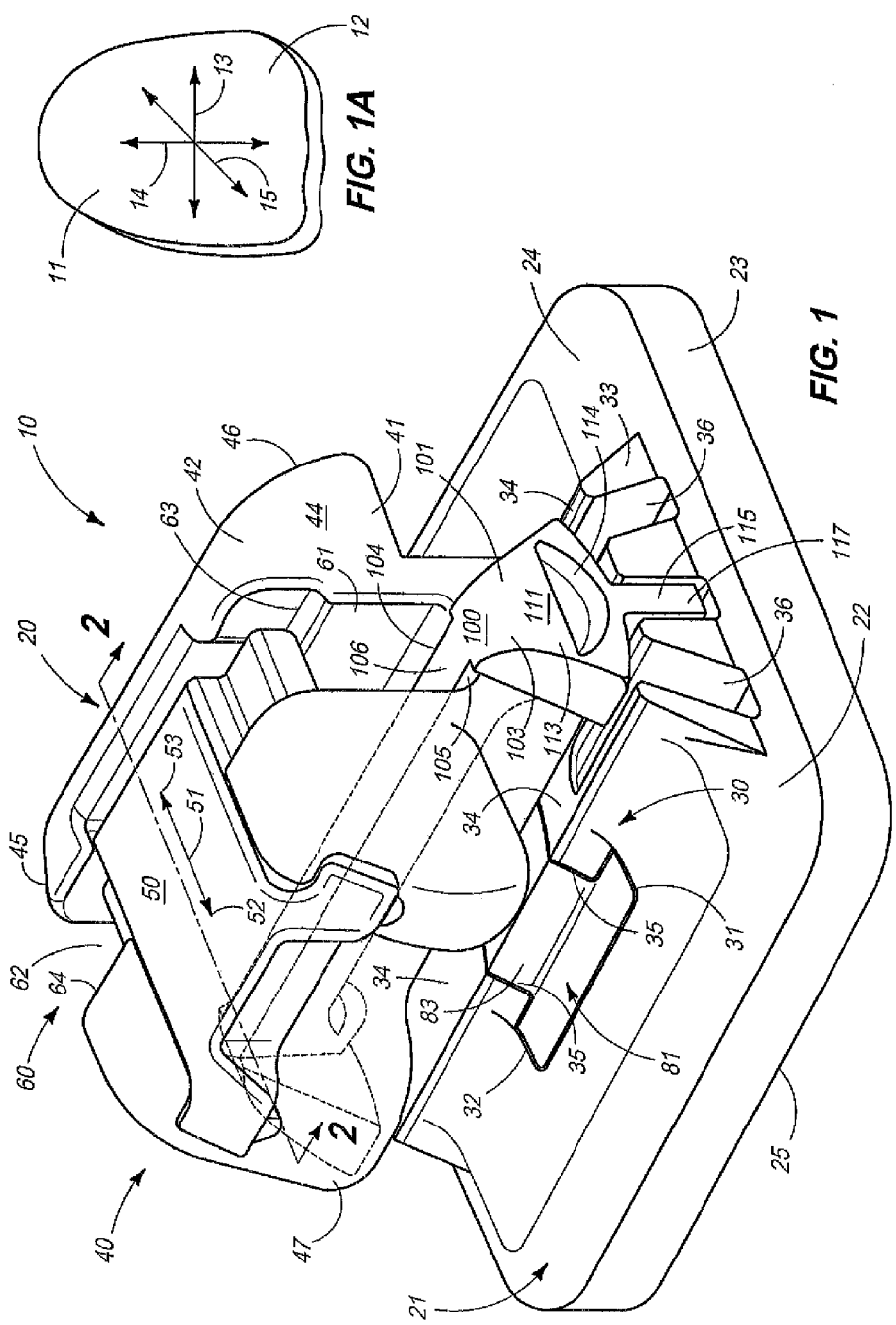
FIG. 1 is a perspective, side elevation view of one form of the orthodontic bracket of the present invention.
Figure 2:
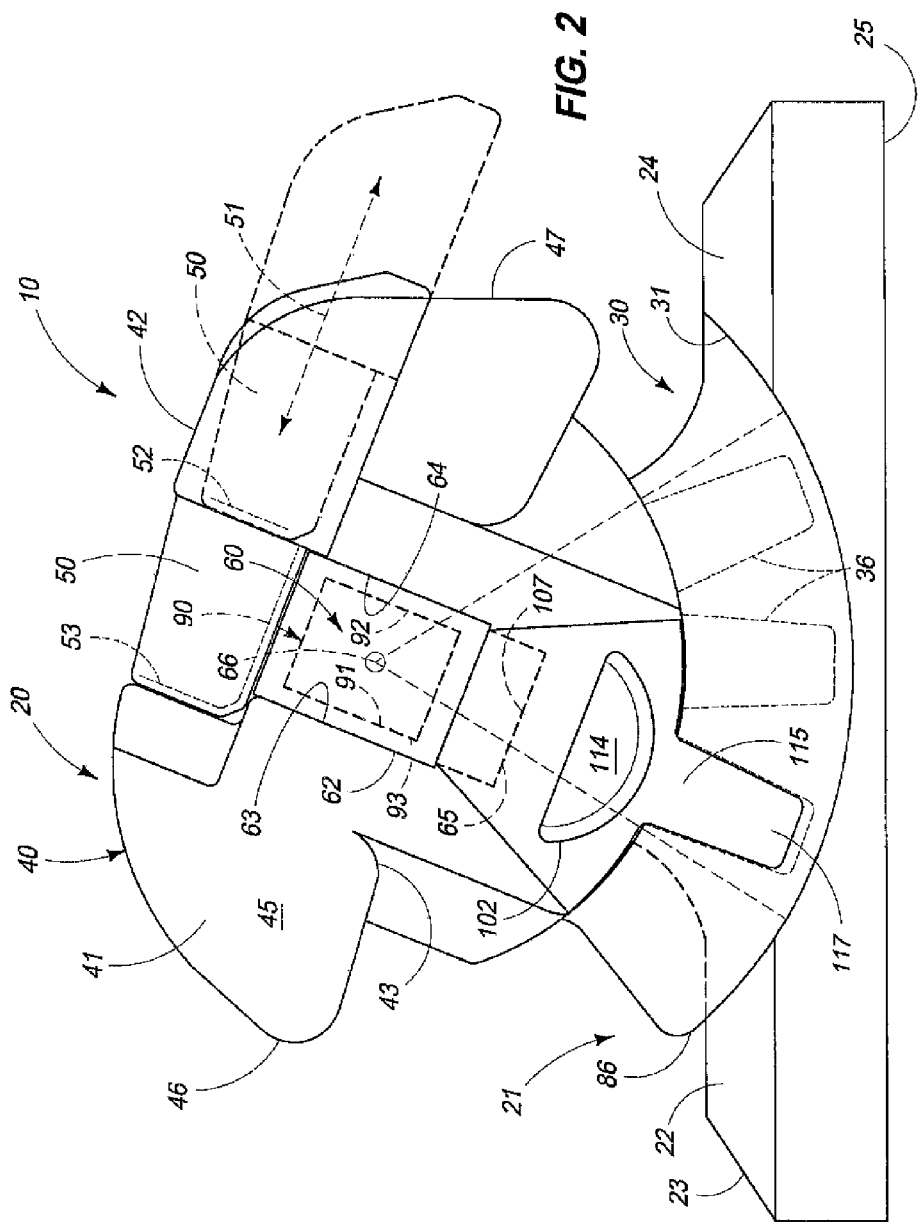
FIG. 2 is a transverse, vertical sectional view of the first form of the orthodontic bracket as seen in FIG. 1, and which is taken from a position along line 2-2 of FIG. 1.
Figure 3:
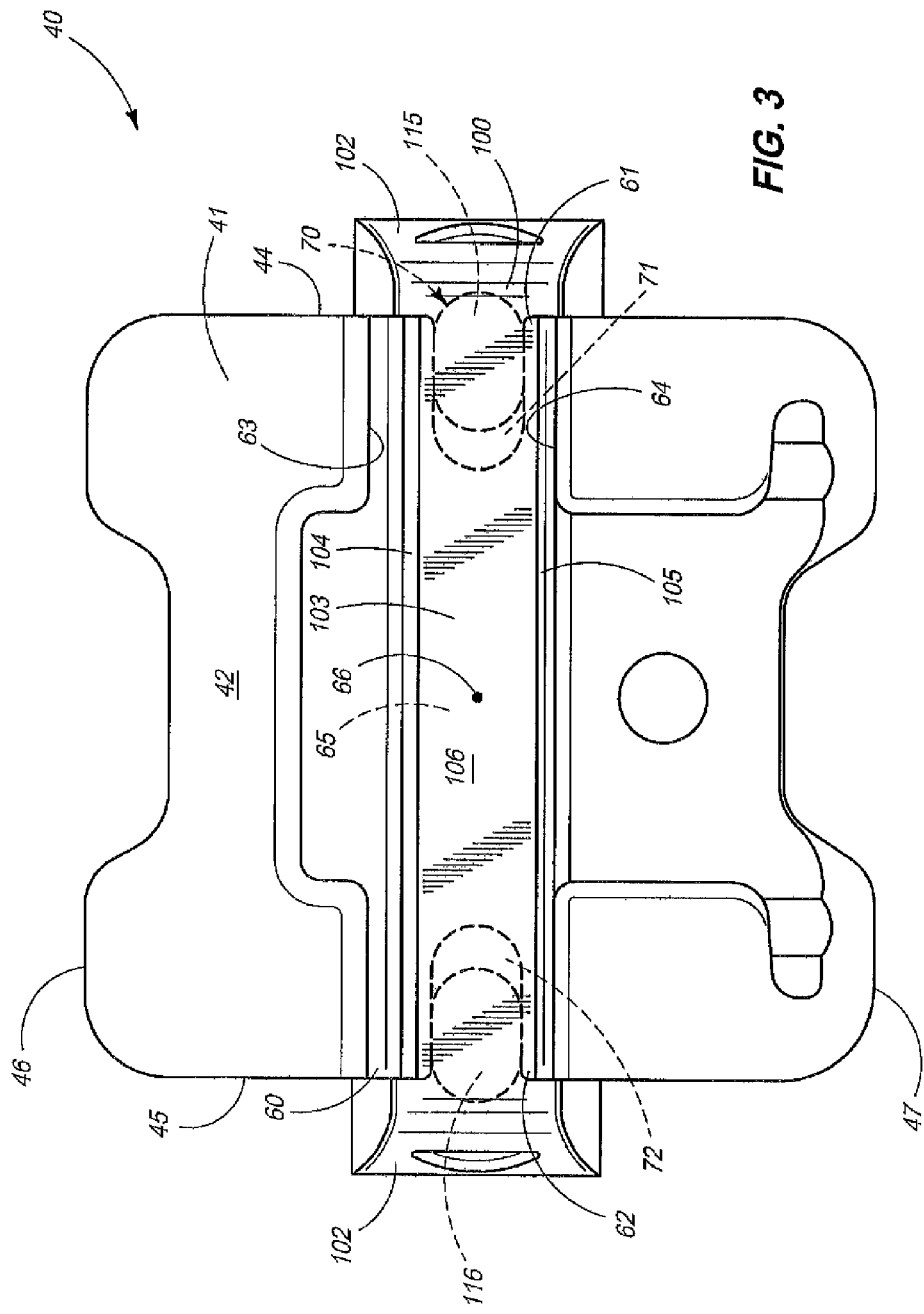
FIG. 3 is an anterior, side elevation view of the first form of the orthodontic bracket as seen in FIG. 1, with the gate removed, to show the structure thereunder.

The present invention, in its various forms, is generally indicated by the numeral 10 in FIG. 1 and following. For purposes of the present application, and for the several forms of the invention as described, hereinafter, it will be understood that the various forms of the invention are employed to be releasably affixed to a patient's tooth 11 as seen in FIG. 1A, and in particular, to the anterior facing surface 12 thereof. The orthodontic bracket 10, in its various forms, and in combination with the arch wire as will be described, hereinafter, is employed to provide a multiplicity of selective torque expressions which individually forcibly act upon the patient's tooth 11. For purposes of this patent application, the term "torque expression" as used hereinafter, is defined as the force which provides rotation of a patient's tooth 11 around the X axis, that being the mesial/distal direction. In particular, the orthodontic bracket 10 of the present invention can be employed to achieve first, second and third order movements, that is 13, 14 and 15, respectively, as seen in FIG. 1A, without a clinically predetermined manipulation, bending, twisting, or other rotation of the rectangularly shaped arch wire, or the often repeated replacement of this same arch wire during the orthodontic treatment period. Further, and as will be discussed later in the application, the treatment of a patient may proceed to completion without the removal of the bracket base, as will be described, from the patient's tooth, although the bracket body which is releasably mounted on the bracket base may be replaced with other bracket bodies during the treatment period based upon the clinical judgment of the treating clinician. The present invention 10 provides a novel means by which a clinician, by utilizing a bracket body insert, as will be described hereinafter, can readily adjust the cross-sectional dimension of an arch wire slot as will be described to achieve first, second, and third order movements of the tooth of a patient and thereby considerably shorten patient treatment times, and also achieve superior treatment results, and increase a patient's comfort in a manner not possible by utilizing the prior art appliances or practices which are known.

First Form of the Invention

As earlier discussed in this application, tooth movement is defined relative to three planes in space. In this regard, movements in these respective planes are categorized as first order, second order, and third order movements, that being, 13, 14 and 15, respectively as seen in FIG. 1A. First order movements 13 are commonly thought of as rotation and/or in and out movements. This refers to movements that can be viewed from the occlusal perspective. On the other hand, second order movements are often referred to as tipping, and can be viewed from a buccolingual or labiolingual perspective. These include movements in the occlusal-gingival direction or tipping about the buccolingual or labiolingual axis. As a general matter, rotation about the aforementioned axes would typically result in tipping of the root or crown of a patient's tooth 11 in a mesial or distal direction. These second order movements are used for paralleling of the roots of the respective teeth 11 as well as elevating or depressing a given tooth. Finally, third order movements 15, and which are commonly thought of as "torque" can be viewed from a mesial-distal perspective or a buccolingual cross-section. Third order movements typically refer to movements about the mesial-distal axis. This particular movement is often important when attempting to achieve proper incisor or labio-lingual or bucco-lingual inclination. First, second, and third order movements, again, are best seen in FIG. 1A, and are indicated by the numerals 13, 14 and 15, respectively. The first form of the invention is generally indicated by the numeral 20 in FIGS. 1-6. In this regard, the first form of the invention 20 includes a bracket base which is generally indicated by the numeral 21, and which further includes a pad 22. The pad 22 is suitably affixed by an adhesive, not shown, to the anterior facing surface 12 of the patient's tooth 11. The bracket base further has a peripheral edge 23, and further is defined by an anterior or outside facing surface 24, and an opposite, posterior facing surface 25 which is attached by the adhesive, not shown, to the anterior facing surface 12 of the patient's tooth 11. As noted earlier, this bracket base typically remains secured to the patient's tooth throughout treatment.

Figure 5:
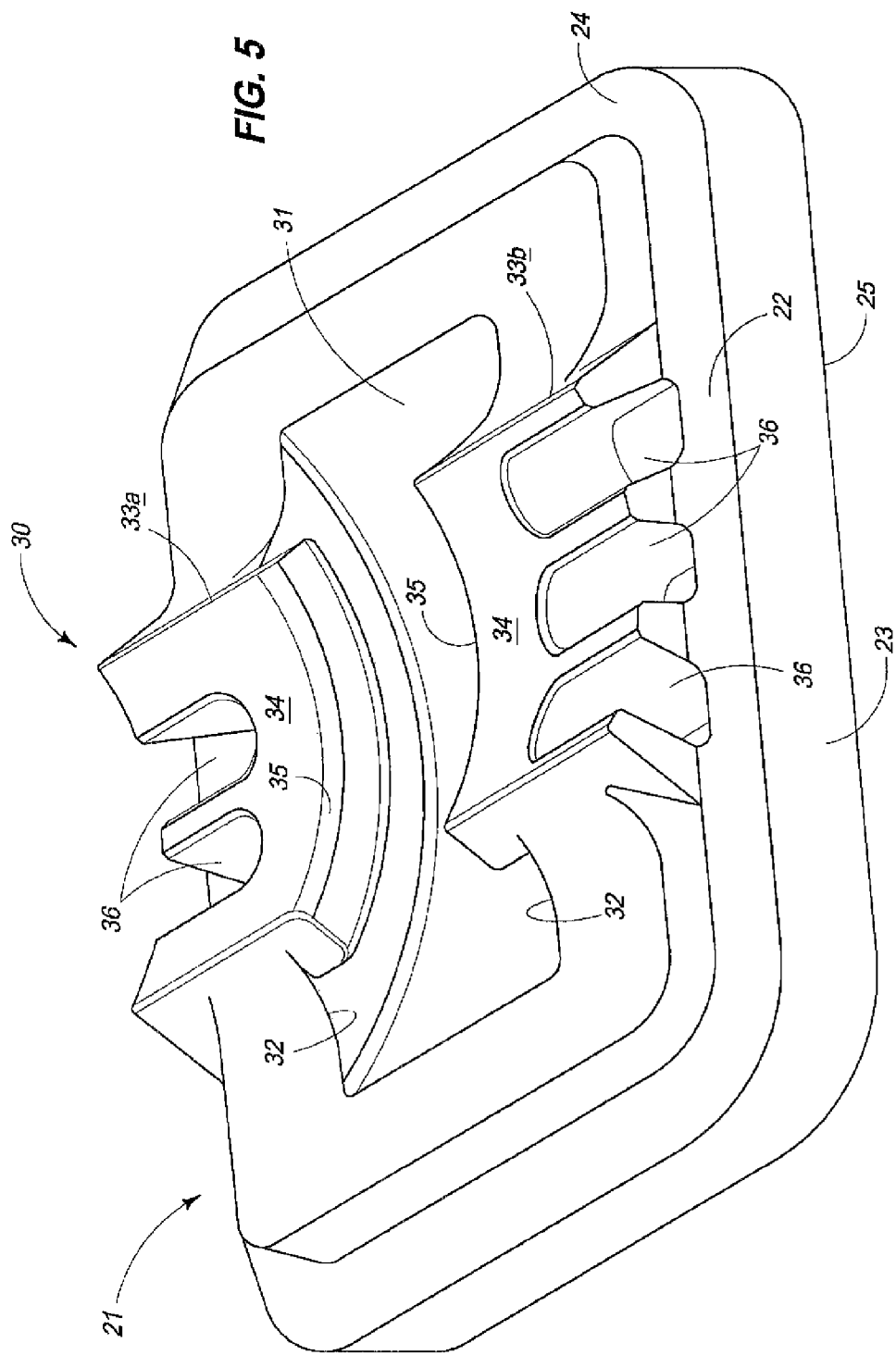
FIG. 5 is a perspective, fragmentary, greatly enlarged side elevation view of a bracket base which finds usefulness in the first form of the orthodontic bracket as best seen in FIG. 1.
Figure 6:
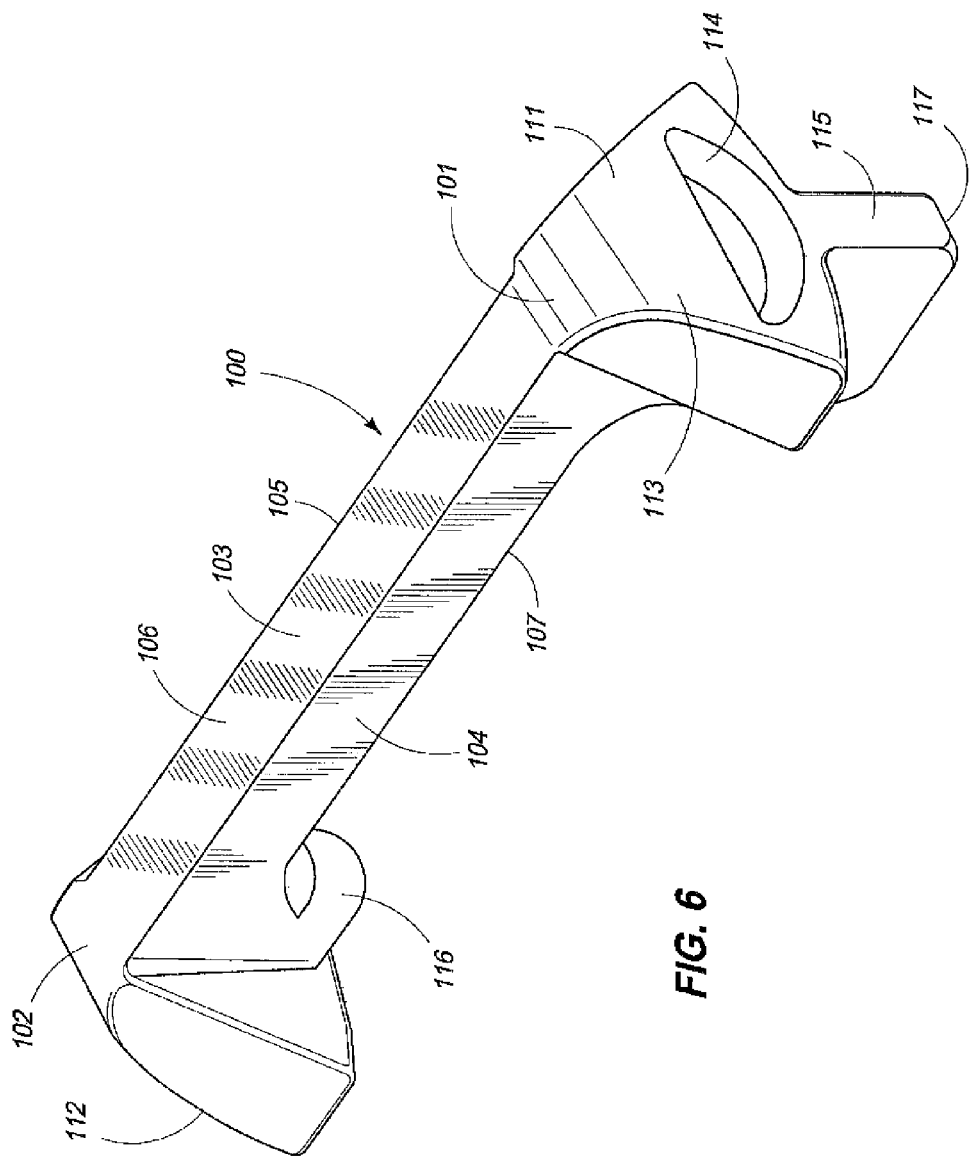
FIG. 6 is a perspective, side elevation view of a bracket body insert which finds usefulness in several forms of the orthodontic bracket as seen in the present application.
Figure 7:
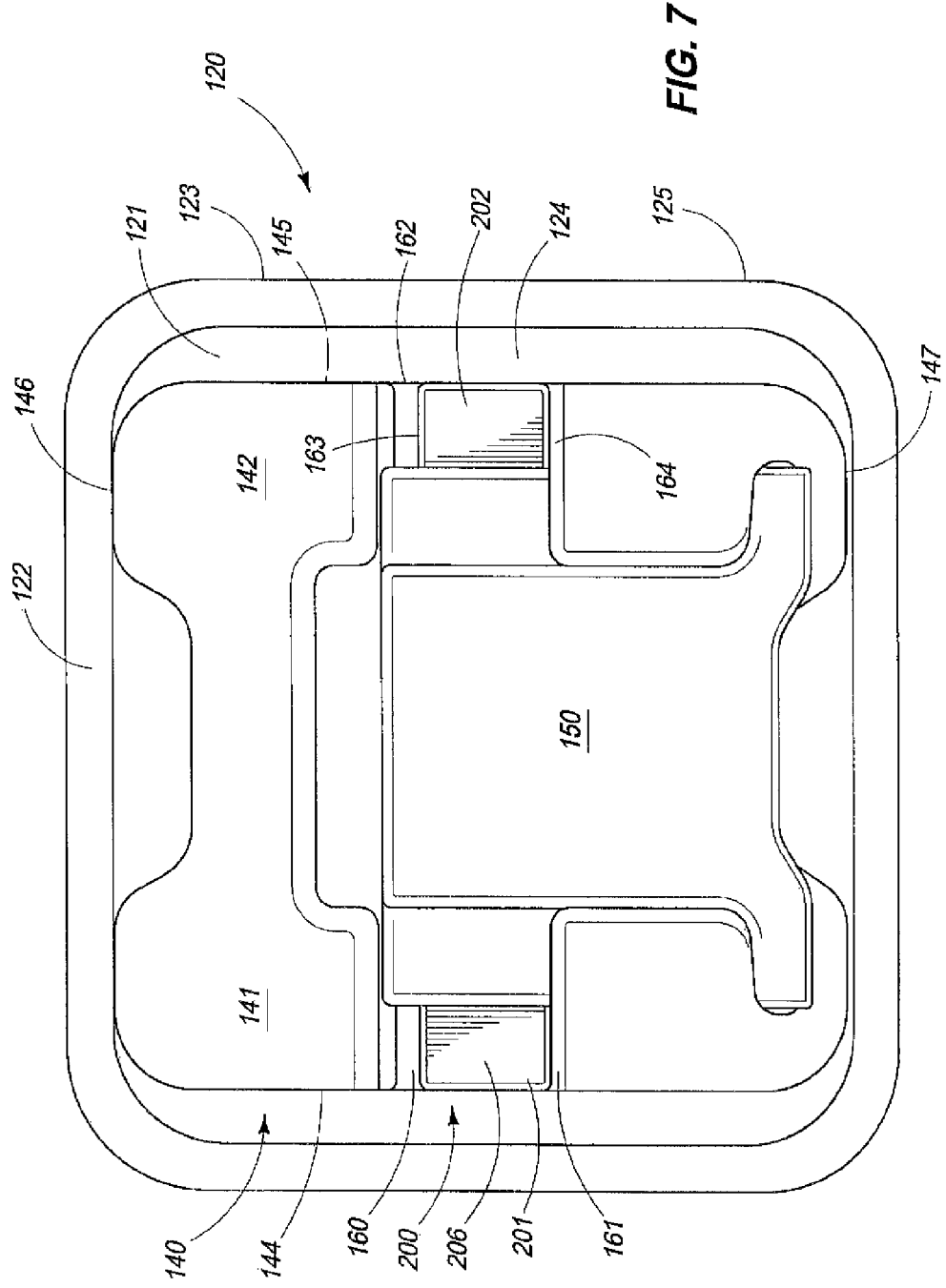
FIG. 7 is an anterior facing, side elevation view of a second form of the orthodontic bracket of the present invention.
Figure 8:
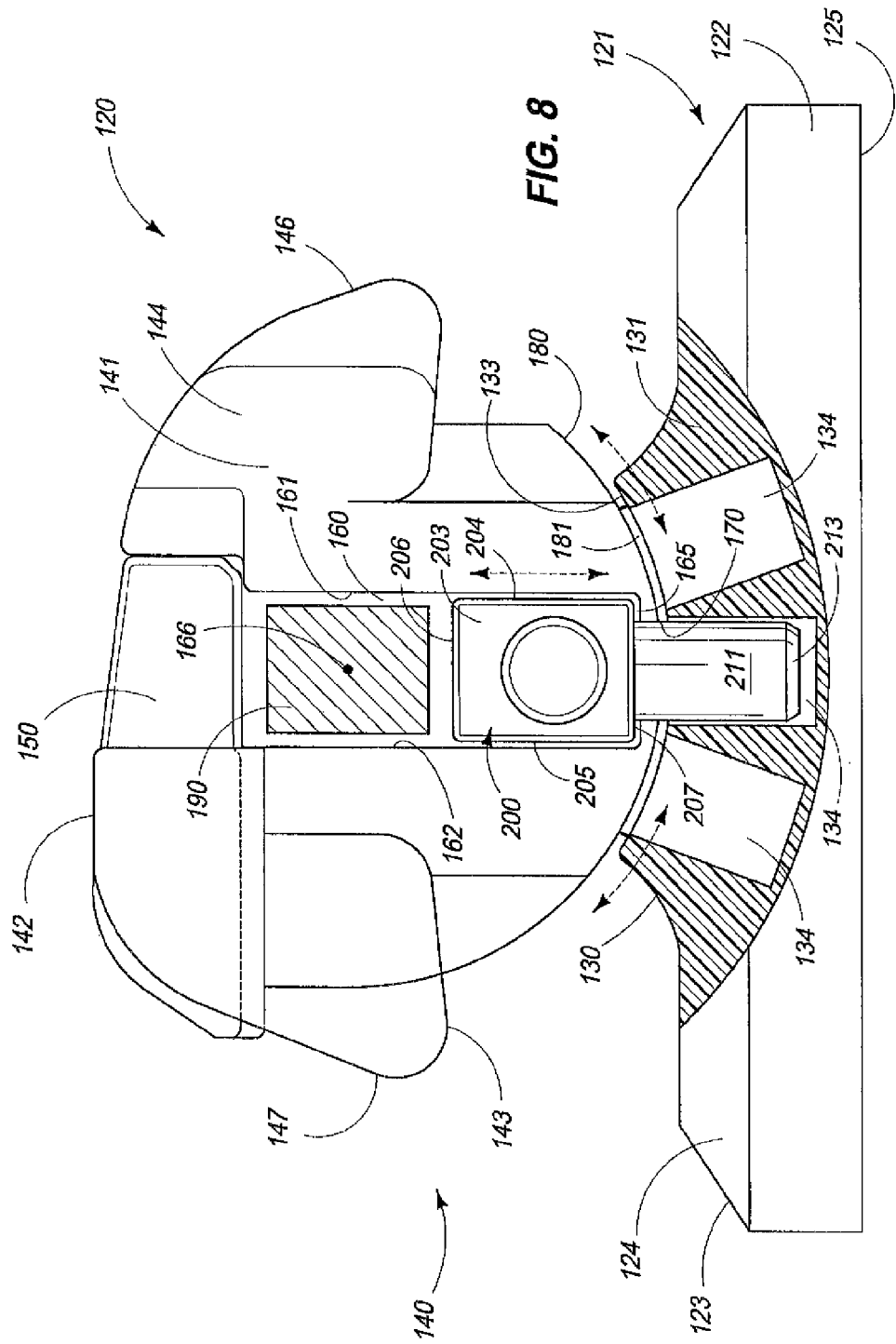
FIG. 8 is a mesial, side elevation view of the second form of the orthodontic bracket as seen in FIG. 7.
Figure 9:
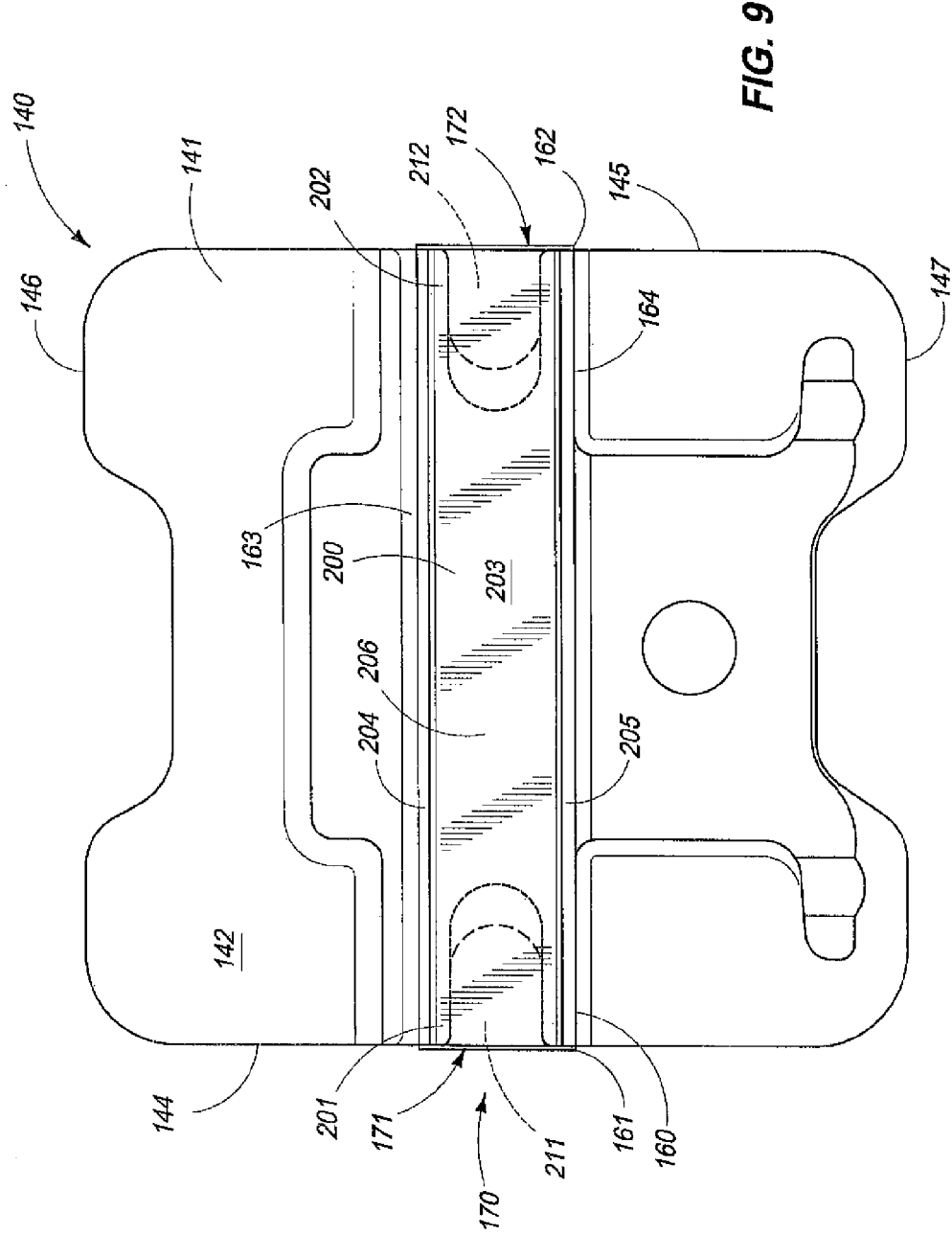
FIG. 9 is an anterior, side elevation view of the second form of the orthodontic bracket, with the gate removed, to show the structure thereunder.

Referring now to FIG. 5, the first form of the invention 20, and more specifically the anterior facing surface 24 of the bracket base 21 includes a coupling portion or region which is generally indicated by the numeral 30. The coupling portion or region 30 is defined, in part, by a curved dove tailed shaped slot 31 which is illustrated in FIG. 5 as being substantially concavely shaped. However, and while the form of the invention, as illustrated, shows a concavely shaped dove tailed slot, it is equally feasible that a form of the invention may be fabricated whereby the curved dove tailed shaped slot 31 assumes a convexly curved shape. Therefore, the invention should not be limited to that which is illustrated. It will be recognized therefore, that a curved dove tail shaped slot, either of a convex or concave shape, may be equally employed in the fabrication of the present invention. The described coupling portion renders the bracket base, a "universal" base for use with a multiplicity of bracket bodies, as will be described, hereinafter. In the arrangement as described, the bracket base 21 can be employed with bracket bodies which are considered passive ligation types, active ligation types or conventionally tied brackets. In view of this feature, a clinician no longer has to remove the bracket base when removing and replacing orthodontic brackets. Rather, a clinician must only remove the bracket body from the coupling portion 30, and reattach an alternative bracket body. The bracket base can stay on the tooth for the entire orthodontic treatment time. This feature greatly advances orthodontic practice and makes an orthodontic treatment regimen much more comfortable for a patient. The curved dove tailed slot 31 is defined, in part, by spaced sidewalls 32. Additionally, the coupling portion 30 is defined, in part, by a centrally located, and elevated region 33 having opposite sides, here identified as 33A and 33B, respectively, and which are located on the opposite sides of the curved dove tailed shaped slot 31. The centrally elevated regions 33A and B respectively each have a curved upwardly facing surface 34 having the same curvature as that of the curved dove tailed shaped slot 31. Each of the centrally elevated regions 33 include inwardly extending flange portions 35 which provide a means for slideably, and matingly capturing and cooperating with a moveable bracket body as will be discussed in greater detail, hereinafter. Additionally, and formed in each of the centrally elevated regions 33, and extending downwardly through the curved upwardly facing surface 34 is a multiplicity of engagement regions which are generally indicated by the numeral 36. The engagement regions are utilized to receive, and cooperate with a bracket body insert as will be described in greater detail in the paragraphs which follow. It will be noted from studying FIG. 5 that the multiplicity of engagement regions 36 are disposed in a predetermined spacial pattern which provides a convenient means for adjustably positioning the rotatable orientation of a bracket body and which will also be discussed, below.

The orthodontic bracket 20 as illustrated in FIGS. 1-6 has a moveable bracket body 40 which is borne on the bracket base 21. In this regard, the bracket body 40 has a main body 41 which is defined, in part, by an anterior facing surface 42, and an opposite, posterior facing surface 43. Still further, the bracket body is defined by opposite first (mesial) and second (distal) sides 44 and 45, respectively, and which are located at a predetermined distance, one relative to the other. Yet further, the bracket body 40 includes a superior facing surface 46, and an opposite, inferior facing surface 47. The superior and inferior facing surfaces 46 and 47 define respective tie wings which are well known in the art. As seen in FIG. 1-6, the bracket body 40 mounts a moveable gate which is generally indicated by the numeral 50, and which is also well known in the art. The moveable gate 50 is operable to reciprocally travel or move along a path of travel 51 between a first, down or open position 52, and a second up, or occluding position 53 (as seen in FIG. 1). The gate 50, which moveably cooperates with the anterior facing surface 42 of the bracket body 40, is operable to selectively retain an arch wire as will be discussed, below, within a transversely disposed arch wire slot which is generally indicated by the numeral 60. The transversely disposed arch wire slot 60 has a given volume, and further has a first end 61 which is located adjacent to the first, mesial side 44 of the bracket body 40, and an opposite, second or distal end 62 which is located adjacent to the second side 45. The arch wire slot 60 is defined, at least in part, by a top, or superior surface 63, and an opposite, bottom or inferior facing surface 64. The top and bottom surfaces which define, in part, the arch wire slot 60 are disposed in substantially parallel, spaced relation one relative to the other. The given distance allows the arch wire slot 60 to receive an arch wire as will be described, hereinafter. Still further, the main body 41 defines a supporting rear wall 65 (FIG. 2) which extends between the top and bottom surfaces 63 and 64, but which does not define the resulting arch wire slot 60, as more fully described, below. The arch wire slot 60 has a central region or portion which is indicated by the numeral 65. The arch wire slot 60 is moveable in both the vertical and horizontal planes as will be described, below. This rotation of the arch wire slot in either of the vertical or horizontal planes is maintained about the central region 66 of the arch wire slot 60. This feature of the invention provides huge benefits and advantages to a clinician who is employing the invention. In the arrangement as seen in the drawings, it should be understood that the arch wire slot 60 as more fully described below, has a predetermined cross-sectional dimension which is variable by means of a bracket body insert as will be discussed in greater detail, hereinafter, and which fills or occupies at least a portion of the volume of the arch wire slot 60. This is in contrast to that which is described in our co-pending U.S. patent application Ser. No. 13/745,638.

Figure 4:
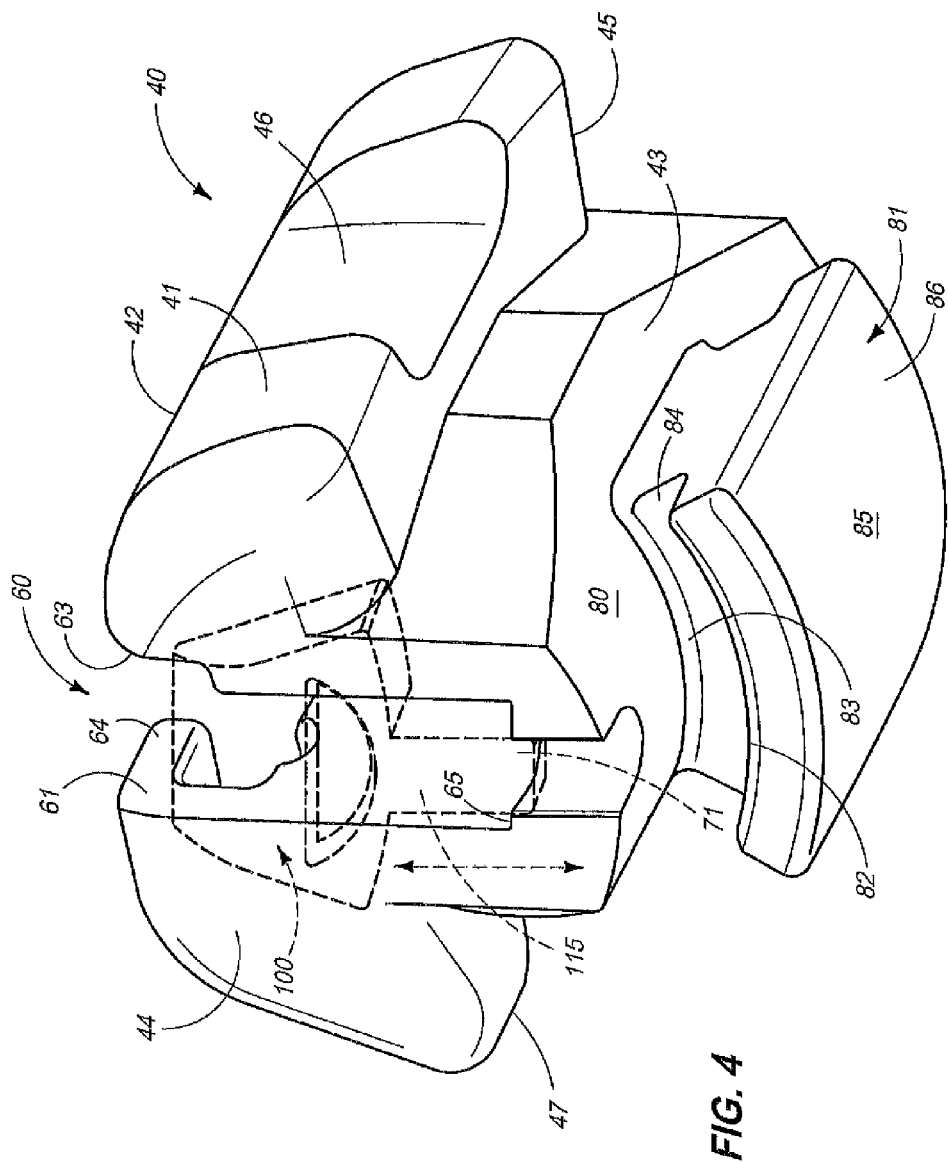
FIG. 4 is a fragmentary, perspective, side elevation view of a bracket body which forms a feature of the first form of the orthodontic bracket as seen in FIG. 1.

The orthodontic bracket 10, as described, and more specifically the first form 20 thereof, includes a bracket body 40 having a posterior facing surface 43, and wherein the posterior facing surface 43 has a complimentary, substantially uniformly curved surface which matingly, and moveably engages the coupling portion 30 of the bracket base 21. As earlier described, the coupling portion 30 of the bracket base 21 defines a curved dove tailed shaped slot 31 having a predetermined shape, and dimensions, and the bracket body 40 further includes a complimentary uniformly curved surface 80, and a movably mating structure which moveably and matingly engages the coupling portion of the bracket base as seen in FIG. 4. This complimentary, substantially uniformly curved surface 80, which forms the posterior facing surface 43 moveably cooperates with the curved upwardly facing surface 34 of the centrally elevated region 33, and which further forms a feature of the coupling portion 30. The bracket body 40 also includes a curved, male pin member 81 forming the aforementioned structure and which is made integral with the substantially uniformly curved posterior facing surface 80 of the bracket body 40, and which is further dimensioned for complimentary, slideable, matingly engageable receipt within the curved dove tailed shaped slot 31 which is formed in the bracket base 21. This feature provides a means by which various bracket bodies can be designed to matingly cooperate with the bracket base 21. This, of course, allows the bracket base to remain attached to the tooth 11 throughout the orthodontic treatment. As will be understood, rotation of the bracket body 40 relative to the bracket base 21 is effective in moving the male pin member 81 along the curved dove tailed shaped slot 31 which is formed in the bracket base 21. The male pin member 81 is defined by a main body 82 which includes a central support post or shaft region 83, and which is located, or otherwise received within the space that is defined between the flange portions 35, and which further form the centrally elevated region 33. The central support portion or shaft 83 has a distal end 84. Made integral with the distal end 84 is an enlarged, transversely disposed flange portion 85. The flange portion 85 has a width dimension which is less than the distance as measured between the sidewalls 32, and which individually form a portion of the curved dove tailed shaped slot 31. Further, this same flange portion 85 has a thickness dimension which is less than the distance as measured between the flange portions 35, and the curved dove tailed shaped slot 31. In its curved configuration, the enlarged flange 85 has a complimentary curved surface 86 which has a curvature which is similar to that provided for the curved dove tailed shaped slot 31. As dimensionally designed, the male pin member 81 matingly interfits or otherwise cooperates and slides along the curved dove tailed shaped slot 31 thereby rendering the bracket body 40 rotatable within the curved dove tailed shaped slot 31. Additionally, this feature provides a means by which the bracket body can be readily detached from the bracket base, and be replaced with another form of a bracket base in order to achieve several additional clinical advantage desired by the treating physician. When the bracket base 21 is appropriately attached to the patient's tooth 11, the transversely disposed arch wire slot 60 has a vertical orientation relative to the bracket body 40, and the arrangement as provided with this invention permits the individual torque expressions, here indicated as being first, second and third order movements 13, 14, 15, respectively, to be readily adjusted without significantly impacting the vertical orientation of the transversely disposed arch wire slot 60. This is best seen by reference to FIG. 2. This is a significant advancement in the prior art inasmuch as the rotation of the bracket body 40 relative to the bracket base 21 does not vertically adjust the transversely disposed arch wire slot while different torque expressions are provided for moving the patient's tooth 11. This is a significant advantage over our previously disclosed invention as seen in co-pending application Ser. No. 13/745,638.

As illustrated in the drawings, the orthodontic bracket 10, and in particular, the first form of the invention 20, receives an arch wire 90 which is received within the arch wire slot 60. The arch wire 90 is of traditional design, and is further defined by opposite top and bottom surfaces 91 and 92, and sidewalls 93 which connect the top and bottom surfaces together, and which form a substantially rectangular cross-section. In the arrangement as seen in the drawings, the arch wire 90 is received within the transversely disposed arch wire slot 60, and the bracket body 40 acting in combination with the arch wire 90, is adjustable in both the horizontal or vertical planes so as to provide a multiplicity of selective torque expressions 13-15, respectively, and which individually forcibly act upon the patient's tooth 11. The present invention 20 includes a bracket body insert 100, and which is best seen by reference to FIG. 6, and which is received in the arch wire slot 60 before the arch wire 90 is received in the arch wire slot 60. The bracket body insert 100 has a first end 101, and an opposite second end 102. The bracket body insert further has an elongated main body 103 which is defined by a top or superior facing surface 104, and an opposite, bottom, or inferior facing surface 105. Still further, the main body 103 is additionally defined by an anterior facing surface 106 which forms a rear wall for the resulting arch wire slot 60, and an opposite, posterior facing surface 107 which rests in juxtaposed resting relation relative to the supporting wall 65, and which is defined by the bracket body 40. The bracket body insert 100 has a height dimension as measured between the top and bottom surfaces 104 and 105 which is less than the distance as measured between the top and bottom surfaces 63 and 64, and which occupies a portion of the volume of the arch wire slot 60 and forms, in part, the resulting arch wire slot 60 which receives the arch wire 90. The height dimension of the main body 103 allows the main body 103 to be received within, the arch wire slot 60, and further rest in mating receipt thereagainst the supporting rear wall 65 which is formed by the bracket body 40. It should be understood that the main body 103 of the bracket body insert 100 may have a substantially constant thickness dimension as measured between the anterior and posterior facing surfaces 106, and 107, or may further have a variable dimension. As such, the bracket body insert 100 provides a convenient means for selectively adjusting the resulting cross-sectional dimension of the arch wire slot 60 so as to provide the benefits of the present invention which include, among others, providing an orthodontic bracket 10 which provides first, second, and third order movements for a patient's tooth 11 without a clinically predetermined manipulation of the arch wire 90 which is received in transversely disposed arch wire slot 60.

The bracket body insert 100 further includes first and second engagement portions 111 and 112, respectively, and which are located at the first and second ends 101 and 102 of the bracket body insert 100. In particular, the first and second engagement portions 111 and 112 extend outwardly beyond of the first and second sides 44 and 45 of the bracket body 40, and further provide a convenient means by which a clinician (not shown) may easily, visually identify the bracket body insert 100 such that it may be positioned appropriately or otherwise adjusted as will be discussed in further detail, below. Each of the engagement portions 111 and 112 respectively, have an outside facing surface 113 which has formed therein a depression or cavity 114 which allows a clinician to insert a tool like tweezers or the like in the depression in order to conveniently remove the bracket body insert 100 from the arch wire slot 60. As will be seen in FIG. 6, the bracket body insert 100 also includes a first, engagement member 115 which extends normally, downwardly relative to the first end 101 of the bracket body. The first engagement member is dimensioned so as to be slideably received within the first passageway 71 which is formed in the first side 44 of the bracket body 40. Still further, the bracket body insert 100 includes a second engagement member 116, which is shorter in length than the first engagement member 115, and which further is received in the second passageway 72, and which is formed in the second side 45 of the bracket body 40. The first engagement member 115 has a distal end 117 which is operable to be matingly received within one of the multiplicity of engagement regions 36 which are formed in the bracket base 21. As will be recognized, when the main body 103 of the bracket body insert 100 is appropriately inserted within the arch wire slot 60, the distal end 117 of the engagement member 115 is received within one of the multiplicity of engagement regions 36, and thereby is effective in fixedly, rotatably positioning the bracket body 40 in an appropriate rotatable orientation relative to the bracket base 22. Further, and as will be recognized from later drawings (FIGS. 19A-C), the main body 103 of the bracket body insert can be fabricated in different thickness dimensions and consequently, provides a means once it is received within the arch wire slot 60 by which the orthodontic bracket 20 can be provided with a resulting arch wire slot 60 having a selectively variable cross-sectional dimensions in order to achieve the benefits of the present invention. Further, it will be recognized by reversing the direction of the main body 103, within the arch wire slot 60, the same bracket body insert 100 can appropriately position the bracket body 40 in five possible, and different, angular orientations relative to the bracket base 21, so as to provide a multiplicity of treatment options for a clinician employing the same orthodontic bracket 20 to correct the misalignment of a patient's tooth 11.

In its broadest aspect therefore, the present invention 10 relates to an orthodontic bracket which, in the first form 20 includes, a bracket base 21 which is releasably affixed to an anterior facing surface 12 of a patient's tooth 11. The invention also includes a bracket body 40 and which is borne on the bracket base 21, and which further has an anterior facing surface 42 which defines a transversely disposed arch wire slot 60 and which further has opposite first and second ends 61 and 62, respectively. The arch wire slot 60 has a selectively adjustable cross-sectional dimension. The present invention 20 further includes an arch wire 90 which is received within the transversely disposed arch wire slot 60. The bracket body 40, acting in combination with the arch wire 90, is adjustable in both horizontal and vertical planes so as to provide a multiplicity of selective torque expressions which individually forcibly act upon a patient's tooth 11. As earlier noted, this movement of the arch wire slot in either the vertical or horizontal planes takes place substantially about the central region 66 thereof. As earlier discussed, the orthodontic bracket 20 can be employed to achieve first, second and third orders of movement 13, 14 and 15, respectively, of the patient's tooth 11 without a clinically predetermined manipulation of the arch wire 90 which is received in the transversely disposed arch wire slot 60. As understood from a study of the drawings, and as noted, above, the transversely disposed arch wire slot 60 has a vertical orientation relative to the bracket body 40. The respective torque expressions as described above can be readily adjusted without significantly impacting or changing the vertical orientation of the transversely disposed arch wire slot 60 relative to the bracket base 21. Stated in another way, the rotational axis of the bracket body 40, is about the central portion 66. Again, this movement provides significant advantages to the treating clinician.

As illustrated in the drawings, the bracket body 40 is shown in the first form of the invention 20 as being partially, rotatably moveable relative to the bracket base 21 in a given axis of movement, here shown in a vertical direction when the bracket base 21 is mounted on the anterior facing surface 12 of the patient's tooth 11. In the first form of the invention 20, the arch wire slot 60 is located in a fixed orientation relative to the bracket body 40. This is in contrast to the second form of the invention as will be discussed, hereinafter and wherein the arch wire slot is selectively movably adjustable relative to the bracket body as will be discussed, hereinafter. As noted above, the cross-sectional dimension of the arch wire slot 60 is defined by opposed, and predetermined, spaced top and bottom surfaces 63 and 64, and a rear wall 65 which extends between the top and bottom surfaces 63 and 64 of the arch wire slot 60. However, when the bracket body insert 100 is received in the arch wire slot 60, the anterior facing surface 106 of the bracket body insert 100 acts or becomes the rear wall of the resulting arch wire slot 60 and which receives the arch wire 90. In this arrangement the anterior facing surface 106 is selectively adjustable relative to the spaced top and bottom surfaces 63 and 64 so as to provide the selective cross-sectional dimension for the aforementioned arch wire slot 60. In the of the present invention, the cross-sectional dimension of the arch wire slot 60 may be rendered substantially uniform when measured in a direction which extends between the first and second ends 61 and 62 thereof. However, in an alternative form of the invention, the cross-sectional dimension of the arch wire slot may be rendered non-uniform when measured in a direction extending between the first and second ends 61 and 62 of the arch wire slot 60. Such is best understood by studying FIGS. 19A, B and C, respectively.

The orthodontic bracket 10 as shown in the first form of the invention 20 includes a bracket body insert 100 which is releasably received within the transversely disposed arch wire slot 60, and which further has a main body 103 which forms, at least in part, a portion of the arch wire slot 60 as noted, above by filling or occupying a portion of the volume thereof. The main body 103 of the bracket body insert 100 substantially adjustably fixes the rotatable orientation of the bracket body 40 relative to the bracket base 21. In the form of the invention as disclosed, the main body 103 of the bracket body insert 100, and which forms a portion of the arch wire slot 60, has a uniform dimension. However, as noted above, the main body 103 of the bracket body insert 100, and which forms a portion of the arch wire slot 60, may have a non-uniform dimension. The change in the dimensions of the main body 103 of the bracket body insert 100 provides a convenient means for changing the resulting cross-sectional dimensions of the arch wire slot 60 and which cooperates with the arch wire 90. This change in the dimension of the resulting arch wire slot 60 allows a clinician to impart horizontal movement to the arch wire so as to facilitate one of the orders of movement for the patient's tooth 11. In the form of the invention 20, as illustrated, the bracket base 21 further includes a multiplicity of engagement regions 36 which are formed in a predetermined spacial pattern in the bracket base 21. The bracket body insert 100 has an engagement member 115 having a distal end 117, and which is operable to be received within one of the multiplicity of engagement regions 36 which are formed in the bracket base 21. The receipt of the distal end 117 of the engagement member 115 in one of the engagement regions 36 releasably fixes the rotatable orientation of the bracket body 40 relative to the bracket base 21.

More specifically, the present invention includes, in a first form, an orthodontic bracket 20 having a bracket base 21 which is releasably affixed to an anterior facing surface 12 of a patient's tooth 11, and a bracket body 40 which moveably cooperates with the bracket base 21. The bracket body 40 has an anterior facing surface 42 which defines, at least in part, a transversely disposed arch wire slot 60 which communicates with the anterior facing surface of the bracket body 40. In the first form of the invention, a bracket body insert 100 is provided, and which is further releasably received within the transversely disposed arch wire slot 60, and which further forms, at least in part, a portion of the transversely disposed arch wire slot 60 by occupying a portion of the volume of the arch wire slot 60. The bracket body insert 100 further selectively and adjustably fixes the orientation of the movable bracket body 40 relative to the bracket base 21. In the first form of the invention, an arch wire 90 is received in the transversely disposed arch wire slot 60. The movable bracket body 40, acting in combination with the bracket body insert 100, each respectively engage the arch wire 90 so as to provide a multiplicity of torque expressions which individually forcibly act on the patient's tooth 11, and which further cause first, second and third orders of movement 13, 14 and 15, respectively. These first, second and third orders of movement are achieved typically by utilizing the same arch wire 90. As earlier discussed, the transversely disposed arch wire slot 60 has a cross-sectional dimension, and the bracket body insert 100 is operable to selectively adjust the cross-sectional dimension of the transversely disposed arch wire slot 60 so as to allow a clinician to impart these respective movements to the patient's tooth 11.

As earlier discussed, the bracket body 40 is selectively rotatable along a predetermined path of travel, and in a range of movement which is less than about 60 degrees relative to the bracket base 21 while not substantially impacting a vertical orientation of the transversely disposed arch wire slot 60 relative to the bracket body 40. The orthodontic bracket 20 achieves this operational characteristic by providing a bracket base 21 having, on the one hand, a multiplicity of engagement regions 36 which are formed in a predetermined spacial pattern in the bracket base 21, and by further providing a coupling portion 30 which matingly cooperates with the bracket body 40. The bracket body 40 further has a posterior facing surface 43 which matingly, and moveably engages the coupling portion 30 of the bracket base 21. The coupling portion 30, of bracket base 21, has a predetermined, substantially uniform curvature, and the posterior facing surface 43 of the bracket body 40 has a complimentary, substantially uniformly curved surface 80 which forms a structure that matingly, and moveably engages the coupling portion 30 of the bracket base. In the arrangement as seen in the drawings, the coupling portion 30 of the bracket base 21 defines a curved dove tailed shaped slot 31 having a predetermined shape, and dimensions; and a curved male pin member 81 is provided, and which is made integral with the substantially uniformly curved posterior facing surface 43 of the bracket body 40. The curved male pin member 81 forms a structure which is further dimensioned for complimentary, slideable, matingly engageable receipt within the curved dove tailed shaped slot 31 which is formed in the bracket base 21. The subsequent rotation of the bracket body 40 relative to the bracket base 21 is effective in moving the male pin member 81 along the curved dove tailed shaped slot 31 which is formed in the bracket base 21. As disclosed earlier in this application, it should be recognized that these curved surfaces, and structures as recited may be reversed, in their location, and achieve the same benefits of the present invention.

As will be recognized from the drawings, the engagement regions 36, which are formed in the bracket base 21, are located either on one side, or on both sides of the coupling portion 30. Still further, and in another form of the invention, the engagement regions 36 may be formed directly into the coupling portion 30 of the bracket base 21. In one form of the invention, the transversely disposed arch wire slot 60 is defined, in part, by spaced top and bottom surfaces 63 and 64 as earlier disclosed. Still further, the bracket body insert 100 has an elongated main body 103 which is sized so as to fit within the arch wire slot 60 and further fills or occupies at least a portion of the volume thereof. As earlier disclosed, the main body 103 of the bracket body insert has an anterior facing surface 106 which forms or acts as a back wall of the transversely disposed arch wire slot 60, and which further extends between the top and bottom surfaces 63 and 64 of the arch wire slot 60. The thickness dimension of the main body 103 of the bracket body insert 100 is selectively variable so as to cause the transversely disposed arch wire slot 60 to have a selective predetermined cross-sectional dimension. Consequently, upon receipt of the arch wire 90 within the transversely disposed arch wire slot 60, a clinician can easily cause first, second and third order movements to be imparted to specific patient's teeth 11 thereby providing clinical benefits not possible, heretofore.

Second Form of the Invention

The second form of the invention is best seen in FIGS. 7-11, respectively. The second form of the invention operates, to a large degree, in a very similar fashion relative to the first form of the invention 20. In particular, the second form of the invention 120 includes a bracket base 121 which is formed of a pad 122 having a peripheral edge 123, and which further has an anterior facing surface 124, and an opposite posterior facing surface 125 which is, again, adhesively affixed to the anterior facing surface 12 of a patient's tooth 11. The second form of the invention 120 includes a coupling portion 130 which is best seen by reference to FIG. 10. The coupling portion 130 which is made integral with the anterior facing surface 124, again, defines a curved dove tailed shaped slot 131. The curved dove tailed shaped slot 131 is defined, in part, by inclined sidewalls which are generally indicated by the numeral 132. The curved dove tailed shaped slot 131 is somewhat truncated when viewed in cross-section as best seen in FIG. 10. The coupling portion 130 includes a curved, upwardly facing surface 133 which is operable to matingly cooperate with the bracket body as will be described, below. Further, and as seen in FIG. 10, a multiplicity of engagement regions 134 are formed in the curved upwardly facing surface 133 of the coupling portion 130, and operate in a fashion similar to that described in the first form of the invention 20. Although, it should be noted, that these engagement regions are not accessible from either the mesial or distal side of the bracket base.

The second form of the invention 120, includes a bracket body 140 which is similar to that which was earlier described. The bracket body 140 is moveably borne by the bracket base 121, and further has a main body 141 which has an anterior facing surface 142, and an opposite, posterior facing surface 143. Additionally, the bracket body 140 has a first or mesial side 144, and an opposite, second, or distal side 145. Again, the bracket body has a superior facing surface 146, and an inferior facing surface 147. Again, as earlier described, the second form of the invention has a moveable gate 150 which is operable to reciprocally move along a given path of travel in order to selectively occlude an arch wire slot 160 which is defined, in part, by the bracket body 140. The arch wire slot has opposite first and second ends 161 and 162, respectively, and top and bottom surfaces 163 and 164. The top and bottom surfaces are disposed in predetermined, substantially parallel, spaced relation. Still further, the main body 141 defines a supporting wall 165 which extends between the top and bottom surfaces, and which further is located within the main body 141 of the bracket body. Additionally, the arch wire slot has a central portion or region 166. Located endwardly of the arch wire slot 160 are individual passageways 170, here indicated in the drawings as first and second passageways 171 and 172, and which individually extend posteriorly, inwardly relative to the bracket body 140. The first and second passageways are operable to individually, matingly cooperate, at least in part, with a portion of the bracket body insert as will be described, below. Again, as was described with the first form of the invention 20, the second form 120 has a complimentary substantially uniformly curved posterior facing surface which is generally indicated by the numeral 180. Still further, and made integral with the posterior surface 180 is a male pin member 181 which is similar to that which was earlier described with respect to the first form of the invention 20. Therefore, further discussion regarding its structure is unwarranted. The male pin member 181 has a complimentary curved surface 182 which is operable to be received in interfitted mating, sliding relation within the curved dove tailed shaped slot 131 which is defined by the coupling portion 130 of the bracket base 121. Again, the arch wire slot 160 is operable to receive an arch wire 190 of traditional design. Additionally, the second form of the invention 120 has a bracket body insert which is generally indicated by the numeral 200, and which is received within the arch wire slot 160 before the arch wire 190 is inserted. The bracket body insert has opposite first and second ends 201 and 202, respectively. As will be noted, when comparing the bracket body insert 200 with that of the bracket body insert 100, it will be seen that the main body 203 of the bracket body insert 200 has a length dimension which does not exceed the length of the arch wire slot 160 such that the first and second ends 201, and 202 are substantially flush or co-planar with the mesial and distal surfaces 144, and 145 of the bracket body 140. Therefore, in this form of the invention, the bracket body insert 200, working in combination with the bracket body 140, provides a more aesthetically appealing exterior appearance once the orthodontic bracket 10 is mounted on the anterior facing surface 12 of the patient's tooth 11. The bracket body insert 200, as illustrated, includes a top or superior facing surface 204, and an opposite, bottom or inferior facing surface 205. The distance, as measured between the top and bottom surfaces 204 and 205, represent a height dimension which is less than about the dimension as measured between the top and bottom surfaces 163 and 164 of the arch wire slot 160. Again, as was described with the first form of the invention 20, the main body 203 of the bracket body insert 200 includes an anterior facing surface 206 which forms a rear wall of the arch wire slot 160. Still further, the main body 203 has a posterior facing surface 207 which rests in juxtaposed relation thereagainst the supporting wall 165 which is defined by the main body 141 of the bracket body 140. Again, as was discussed with the first form of the bracket body insert, the relative thickness dimension as measured between the anterior and posterior facing surfaces 206 and 207 may be, on the one hand uniform, or on the other hand may be variable. Because of the variation in the thickness dimension of the bracket body insert, the resulting arch wire slot 160 can have a variable cross-sectional dimension. This variable cross-sectional dimension permits a clinician to readily and easily adjust the torquing couples applied to given patient's teeth 11 to achieve the clinical objectives they have predetermined for a patient's orthodontic treatment plan.

The bracket body insert 200 as used in the second form of the invention 120 again includes a first, and longer dimensioned engagement member 211 which is mounted on the first end 201, and which is further positioned substantially perpendicular relative thereto. Additionally, the bracket body insert 200 includes a second engagement member 212 which extends normally downwardly relative to the second end 202. The first and second engagement members are dimensioned to be slideably received within the individual passageways 171 and 172, which are formed endwardly of the arch wire slot 160. The first, and longer of the engagement members 211 has a distal end 213 which is operable to be releasably, and matingly received within one of the multiplicity of engagement regions 134, and which are formed in the coupling portion 130 of the bracket base 121. When received in one of these engagement regions 134, the bracket body insert 200 is operable to substantially releasably and rotatably fix the moveable bracket body 140 relative to the bracket base 121, thereby achieving the orthodontic benefits as earlier described. Again, the dimensions of the bracket body insert 200 are such that it provides a much more appealing and aesthetically pleasing orthodontic bracket which can be used on a patient's teeth 11.

Third Form of the Invention

Figure 12:
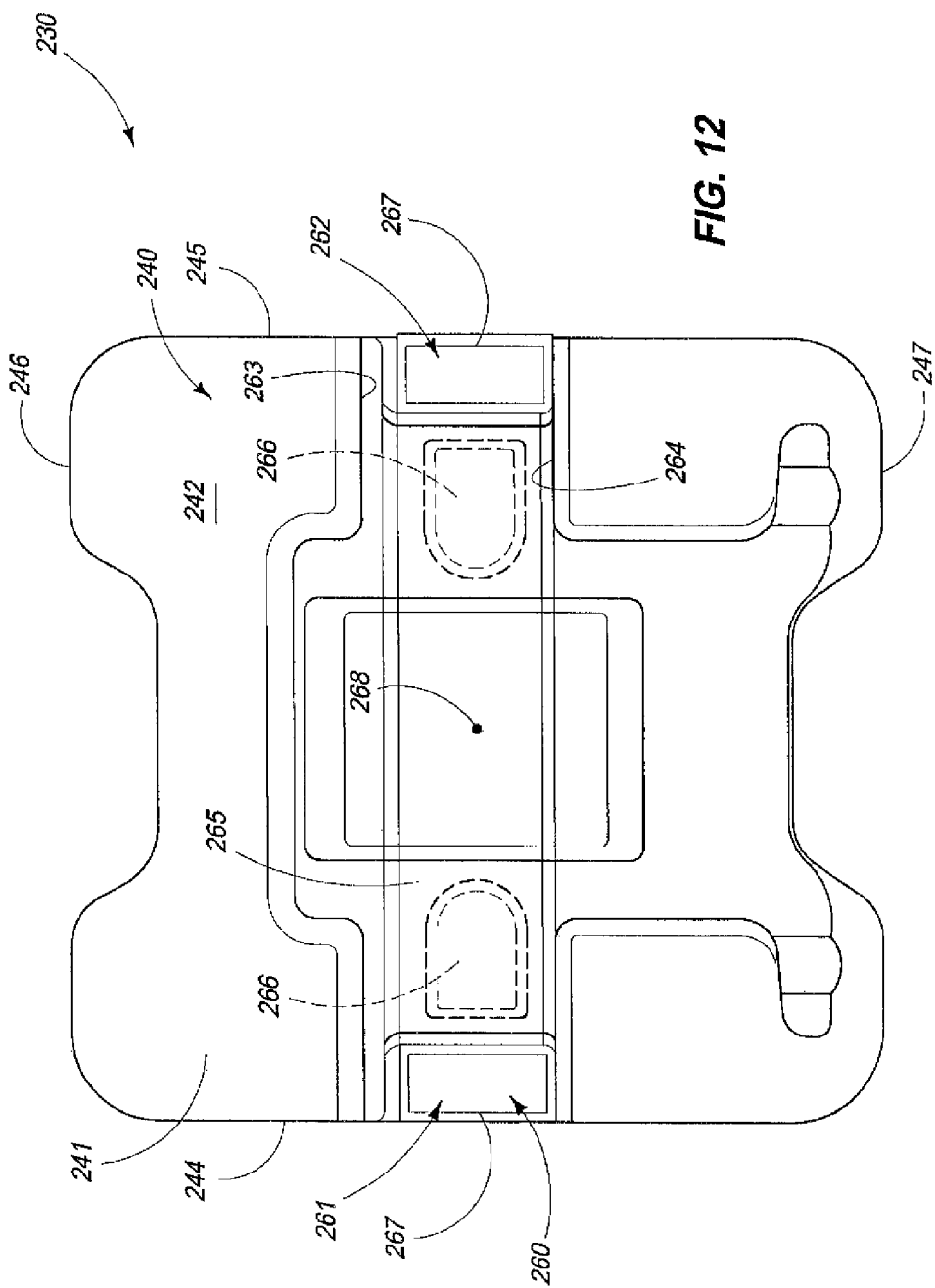
FIG. 12 is an anterior, side elevation view of yet another, third form of the orthodontic bracket of the present invention, and which has the gate removed to show the structure thereunder.

The third form of the invention is generally indicated by the numeral 230 and is best seen in FIGS. 12 and 13, respectively. In the third form of the invention 230, the structure and function is somewhat similar to that described with respect to the first and second forms. Various features of the third form of the invention are therefore not illustrated in the attached drawings so as to expedite an understanding of the present form of the invention. Although it will be understood that structures previously disclosed would be present in a final, completed product. The third form of the invention 230 is similar to the first and second forms 20 and 120, respectively, and has a bracket base including a coupling portion similar to that earlier described. Therefore, repetition of that structure is unwarranted. The third form of the invention as seen in FIG. 12 includes a moveable bracket body 240 which is borne on the bracket base (not shown). The bracket body 240 similarly would include a moveable gate (not shown) for selectively occluding an arch wire slot as will be described, below. However, the gate is removed to show the structure thereunder. The bracket body 240 includes a main body 241 which has an anterior facing surface 242 which is seen in FIG. 12. The bracket body also has a first or mesial side 244, and a second or distal side 245. Again, the main body 241 has a superior facing surface 246, and an opposite inferior facing surface 247. The main body 241 defines, in part, an arch wire slot 260 which is similar to that which is earlier described. The arch wire slot 260 has opposite first and second ends 261 and 262, respectively, and further defines a top and bottom surface 263 and 264 respectively. The top and bottom surfaces are again located in predetermined substantially parallel spaced relation one relative to the other. Again, the main body 241 defines a supporting wall 265 which extends between the top and bottom surfaces 263 and 264, respectively. As seen in FIG. 12, a pair of passageways 266 are formed through the supporting wall 265, and communicate with the posterior facing surface of the bracket body 240. The respective passageways 266 are operable to be substantially coaxially aligned with one of the multiplicity of engagement regions which are formed in the bracket base (not shown), and which allow a bracket body insert, as will be described, below, to engage the supporting bracket base, thereby releasably, rotatably fixing the moveable bracket body 240 relative to the bracket base as was described with the first and second forms of the invention 20 and 120, respectively. As further seen in FIG. 12, it will be noted that individual recessed regions 267 are formed in the main body 241, and are positioned endwardly relative to the arch wire slot 260. Further, the arch wire slot 260 has a central portion or region 268.

Referring now to FIGS. 13A, B and C, respectively, it will be seen that the third form of the invention 230 includes a bracket body insert 300. The bracket body insert has first and second ends 301 and 302, respectively. As will be recognized from the drawings, and as was discussed previously with the second form of the invention 120, the main body 303 of the bracket body insert 300 has a length dimension which is less than about the distance as measured between the opposite first or mesial side 244, and the second or distal side 245. Therefore, the main body 303 may be received within and form a portion of the arch wire slot 260, but will not typically extend beyond the opposite sides of the bracket body thereby providing an aesthetically appealing appearance to the orthodontic bracket 10. The bracket body insert further has a top or superior facing surface 304, and a bottom or inferior facing surface 305. Again, the main body 303 has an anterior facing surface 306 which forms a rear wall of the arch wire slot 260. Again, the thickness dimension of the main body 303 as measured between the anterior facing surface 306, and an opposite posterior facing surface 307 provides a convenient means whereby the bracket body insert 300, once received in the arch wire slot 260, can conveniently, adjustably alter or change the cross-sectional dimension of the arch wire slot so as to provide a convenient means for a clinician to provide selective torquing couples to an arch wire, and thereby provide the many clinical benefits to a patient as was discussed earlier in this application. Similar to the previously described other forms of the invention, the bracket body insert 300 includes a first, and longer engagement member 311 which extends normally downwardly from a location near the first end 301. The first, or longer engagement member 311 is dimensioned so as to be received in one of the passageways 266 which are formed in the supporting wall 265 of the main body 241. The bracket body insert 300 further has a second, or shorter engagement member 312. Again, this second shorter member is located at a position near the second end 302, and which extends normally downwardly therefrom. Again, the second, shorter engagement member, is dimensioned to be received in one of the passageways 266 as earlier described. In this form of the invention 230, the bracket body insert 300 further includes individual movement restraining members 313 which extend normally downwardly from the opposite first and second ends 301 and 302, respectively. The individual movement restraining members are sized so as to be matingly received within the recessed regions 267 which are formed in the main body 241 of the bracket body 240, and which are respectfully located endwardly relative to the arch wire slot 260. As will be recognized in the drawings, the individual movement restraining members 313 have a cavity formed therein. This cavity provides a convenient means whereby a clinician may use a tool such as tweezers, and the like to forcibly engage the bracket body insert 300 and remove it from the bracket body 240. As will be recognized, the thickness dimension of the main body 303 may be varied so as to provide the various torquing couples necessary for appropriate orthodontic treatment. Still further, the bracket body insert 300 may be taken from the bracket body and reversed in direction and then reinserted back in the arch wire slot 260 so as to provide a convenient means whereby the clinician may have a bracket body insert which performs and is able to achieve assorted torquing couples for effective orthodontic treatment of a patent. This feature is common to all the bracket body inserts described in this patent application.

Fourth Form of the Invention

Figure 14:
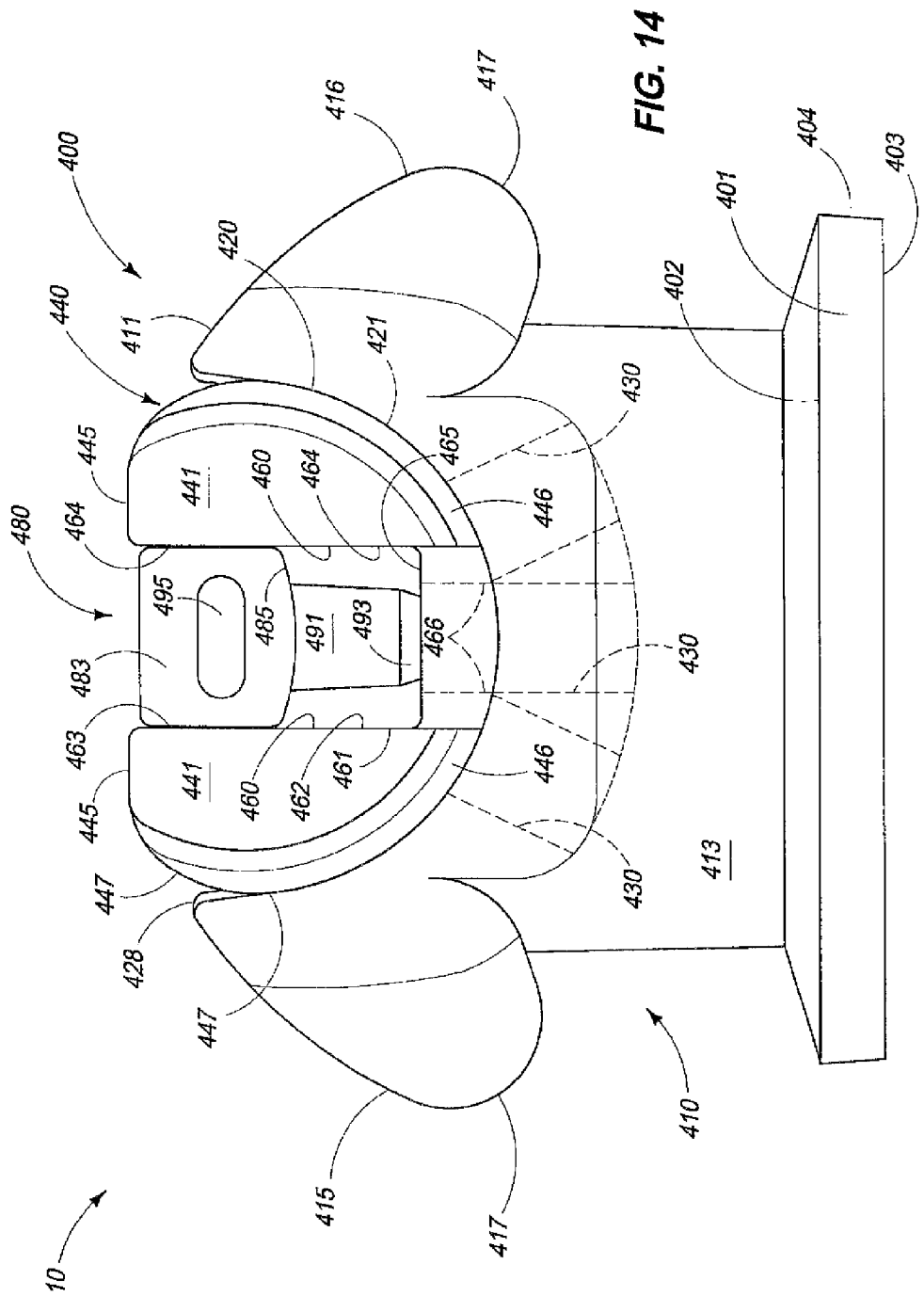
FIG. 14 is a mesial, side elevation view of a fourth form of the orthodontic bracket of the present invention, and which shows a bracket body insert in a first orientation.
Figure 15:
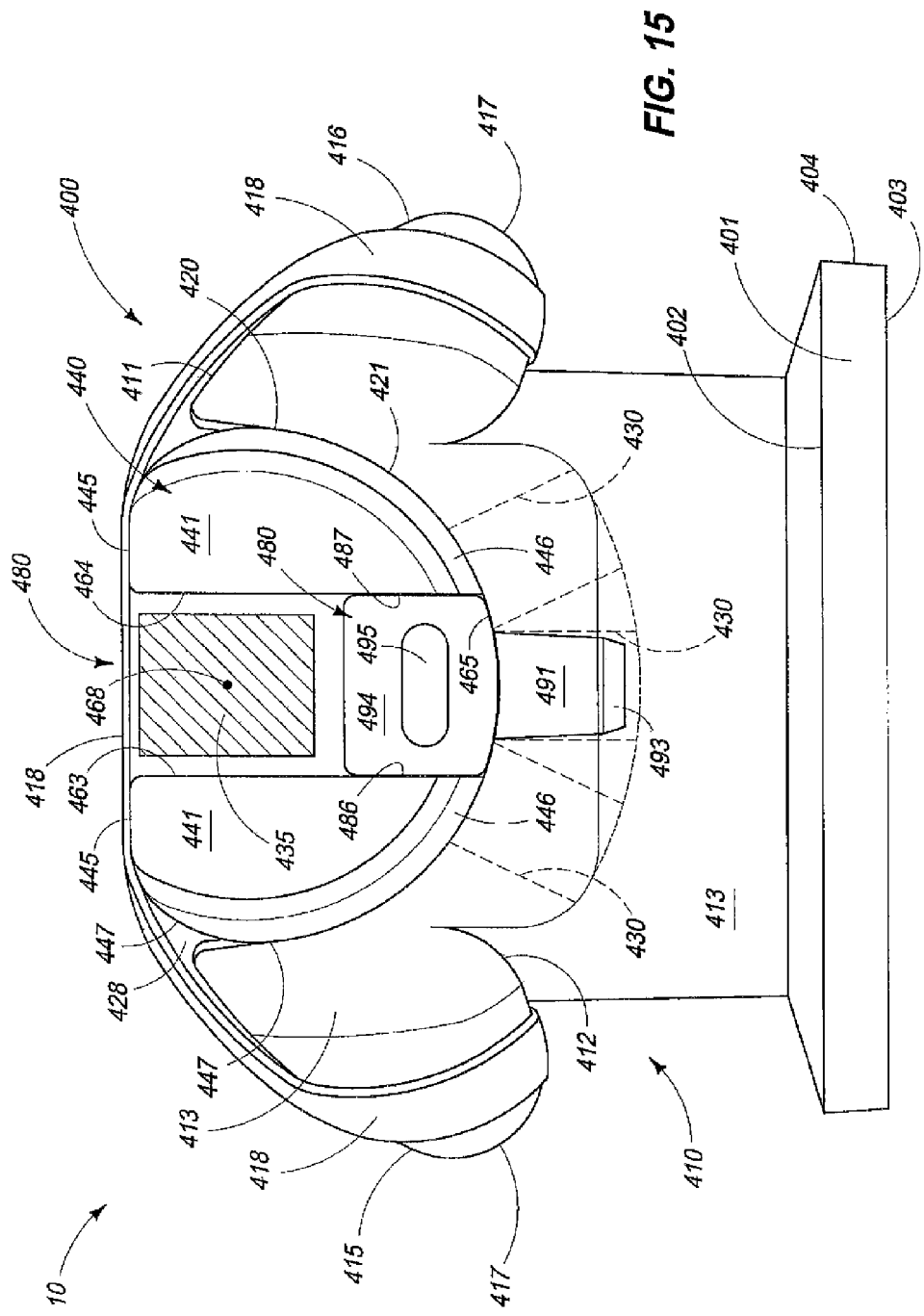
FIG. 15 is a second, mesial, side elevation view of the fourth form of the orthodontic bracket of the present invention, and which illustrates the bracket body insert in a second, operational orientation.
Figure 16:
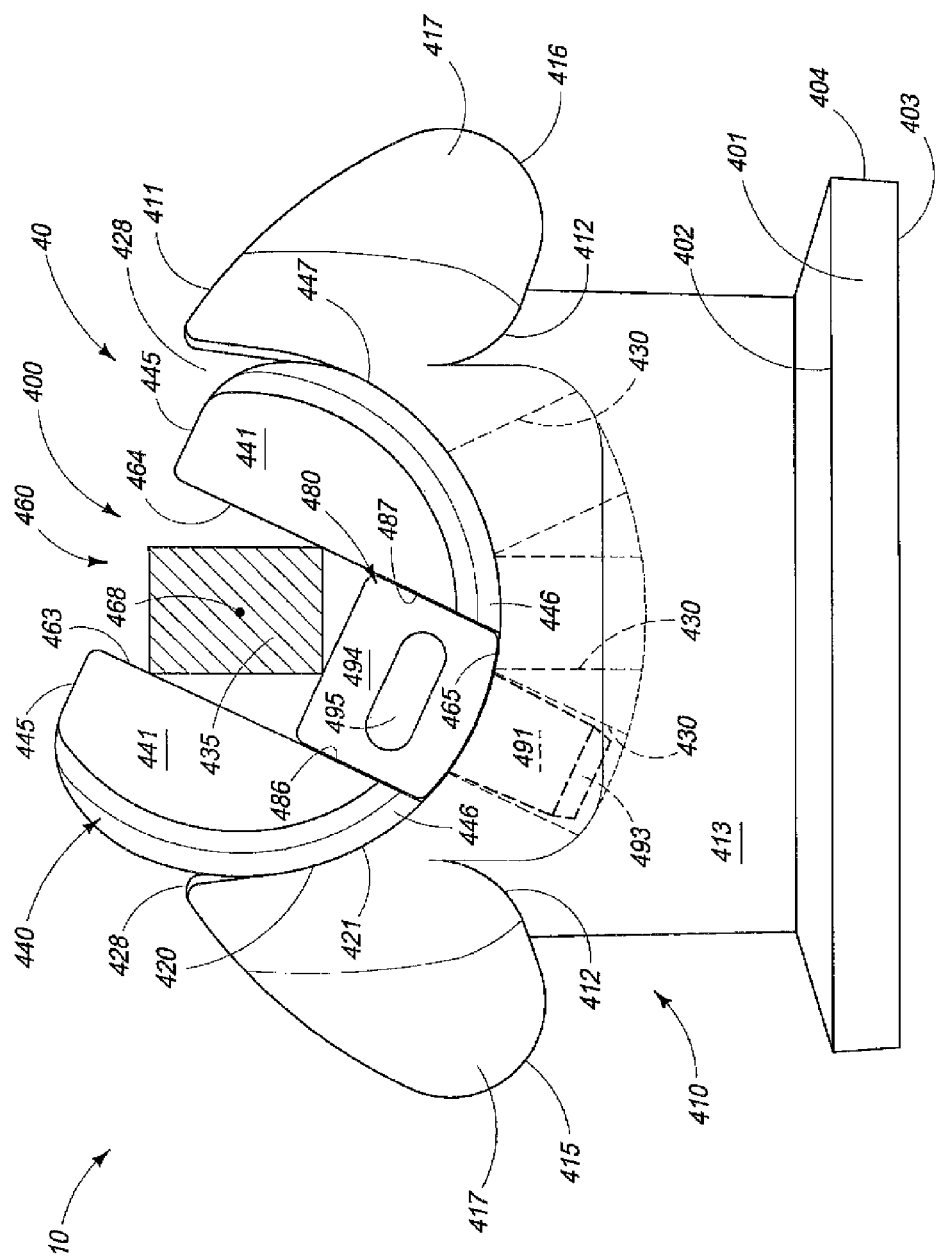
FIG. 16 is yet another, mesial, side elevation view of the fourth form of the orthodontic bracket of the present invention, and which is illustrated in still another operational orientation.

The fourth form of the invention is generally indicated by the numeral 400 and is best seen in FIGS. 14-19, respectively. In the fourth form of the invention, the orthodontic bracket 10, as will be described, includes a bracket base 401 similar to that which was earlier described with the other forms of the invention 20, 120, and 230, respectively. The bracket base 401 has an anterior facing surface 402, and an opposite, posterior facing surface 403 which is suitably adhesively affixed to the anterior facing surface 12 of a patient's tooth 11 to achieve the orthodontic benefits as described in this application. The bracket base further is defined by a peripheral edge 404. As seen in FIG. 14, and following, the fourth form of the invention 400 includes an immovable bracket body 400 which is affixed to, or otherwise made integral with, the bracket base 401. The bracket body 400 has an anterior facing surface 411, and an opposite posterior facing surface 412 which is made integral with the bracket base 401. Still further, the immovable bracket body has a first or mesial side 413, and an opposite or distal side 414. Again, the bracket body 410 includes a superior facing surface 415, and an opposite inferior facing surface 416. The superior and inferior facing surfaces define respective tie wings 417 which are operable to be engaged by a suitable ligature 418 as seen in one of the drawings. The ligature as illustrated is not drawn to scale so as to allow an illustration of the present invention.

Figure 17:
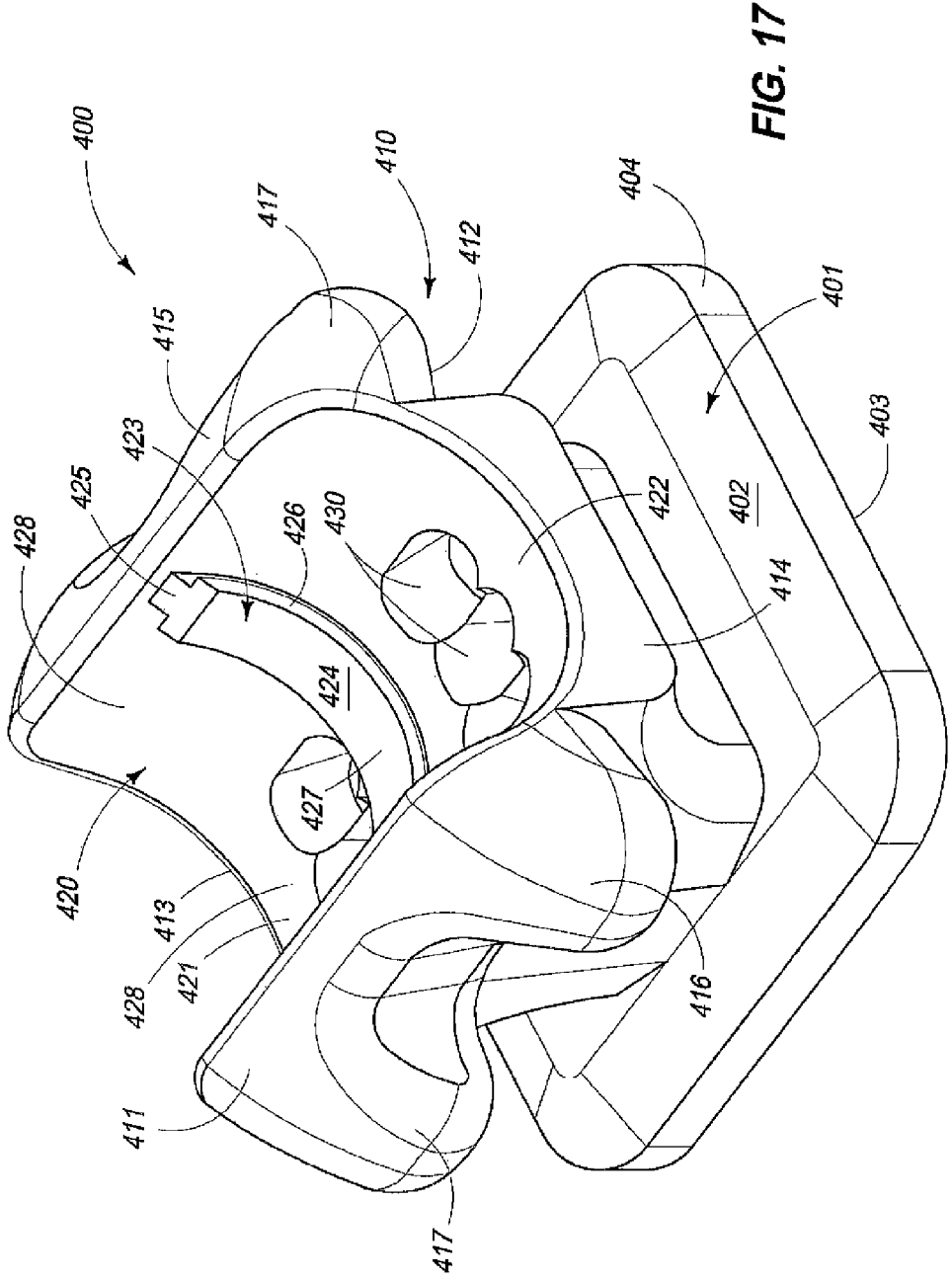
FIG. 17 is perspective, side elevation view of a bracket body which finds usefulness in the fourth form of the orthodontic bracket of the present invention.

The fourth form of the invention 400, and more specifically the immovable bracket body 410, thereof, includes or otherwise defines a transversely disposed, and substantially cylindrically shaped cavity 420 which extends between the first, mesial side 413, and the second, distal side 414. The transversely disposed cavity 420 has opposite first and second ends 421 and 422, respectively. Further, and as best seen in FIG. 17, a curved elongated male pin member which is generally indicated by the numeral 423, is positioned substantially between the first and second ends 421 and 422, and further extends generally radially, inwardly relative to the transversely disposed cavity 420. The curved elongated male pin member is similar in its overall construction, and function, to the male pin member 81 as was described in the first form of the invention 20. In this regard, the curved elongated male pin member 423 is defined by a main body 424 which is made integral with the bracket body 410. The main body 424 further includes a substantially centrally disposed supporting portion or member 425, and further an enlarged flange member 426 is mounted on, or made integral with, the supporting member 425, and extends normally outwardly therefrom to form a substantially T-shaped structure. The enlarged flange member 426 has a curved, upwardly facing surface 427. The curved, elongated male pin member 423 is operable to matingly interfit, and slideably cooperate with a dove tail shaped slot which is made integral with an arch wire insert. This structure will be discussed in greater detail in the paragraphs below. As seen in FIG. 17, a multiplicity of engagement regions 430 are formed in the immovable bracket body 410 and communicate with the transversely disposed substantially cylindrically shaped cavity 420. Again, the multiplicity of engagement regions 430 operate in a similar fashion to that earlier described with respect to the earlier forms of the invention. As will be seen in the drawings, the immoveable bracket body 410 defines an aperture 428 which is formed in the anterior facing surface 411 of the immoveable bracket body 410. The aperture communicates with the transversely disposed cavity 420, and further has a predetermined cross-sectional dimension. This feature will also be discussed in greater detail below.

Figure 18:
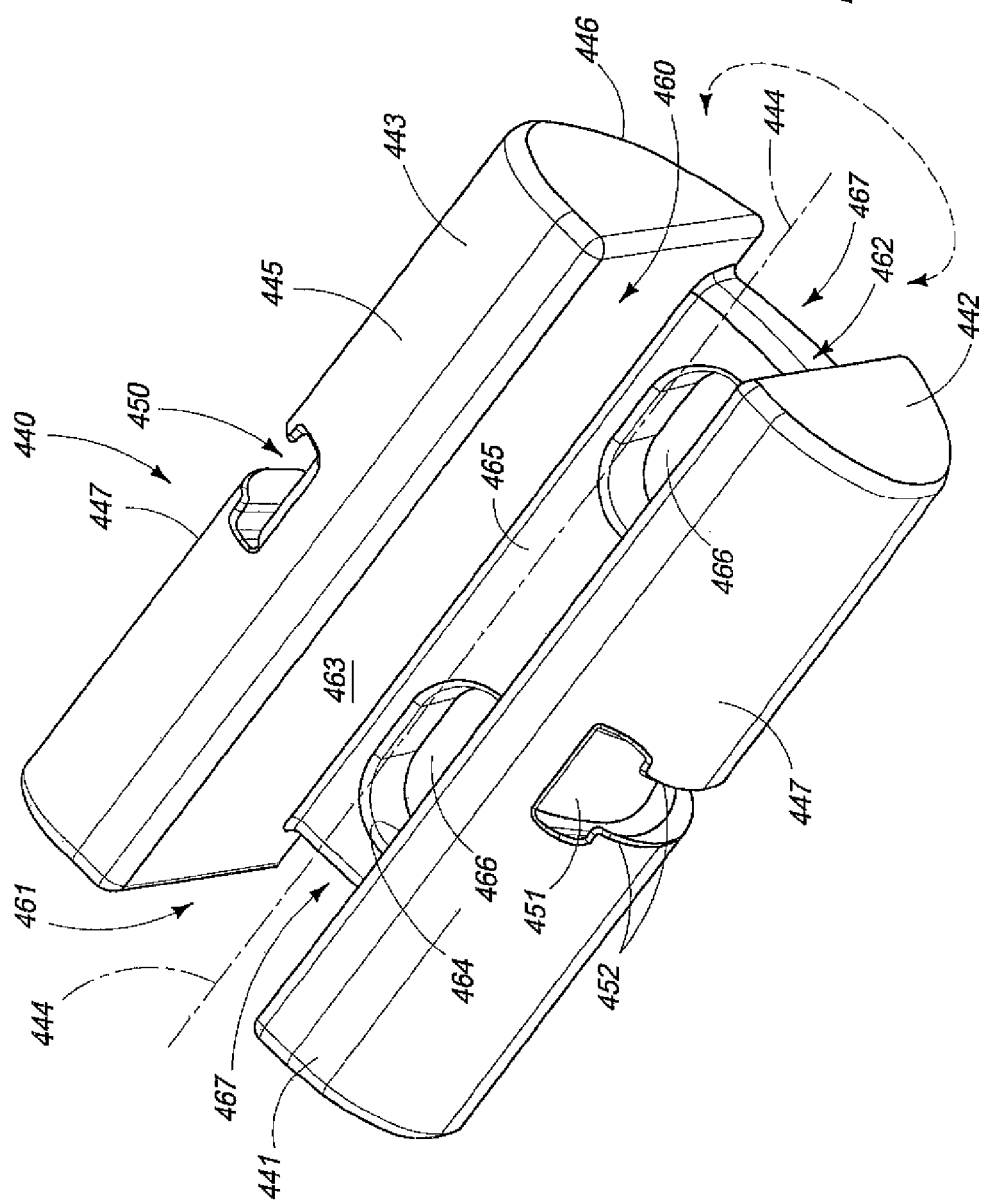
FIG. 18 is a perspective, side elevation view of an arch wire insert which is a feature of the fourth form of the orthodontic bracket of the present invention.

The fourth form of the invention 400 further includes an arch wire insert which is generally indicated by the numeral 440, and which is best understood by a study of FIG. 18. The arch wire insert 440 has opposite ends 441 and 442. The distance between the opposite first and second ends 441 and 442 are equal to or less than the distance as measured between the first, mesial side 413, and the second or distal side 414 of the immoveable bracket body 410. Still further, the arch wire insert 440 has a main body 443 which is defined by a longitudinal axis 444. The main body is dimensioned such that it may not pass out through the aperture 428. However, a portion of the main body 443 extends anteriorly outwardly relative to the aperture 428. The main body 443 is selectively rotatable about the longitudinal axis 444 when the arch wire insert 440 is telescopingly and rotatably received within the transversely disposed cavity 420 as described below. The main body 443 further has an anterior facing surface 445, and an opposite posterior facing surface 446. The main body also has an exterior facing surface 447 which is substantially cylindrically shaped, and which is further dimensioned for rotatable, telescoping receipt within the transversely disposed and substantially cylindrically shaped cavity 420.

As seen in FIG. 18, a curved dove tailed shaped slot 450 is formed in the exterior facing surface 447, and operates in a manner similar to the curved, dove tailed shaped slot 31 as earlier described in the first form of the invention 20. The curved dove tailed shaped slot 450 has a complimentary, curved, bottom surface 451 which slideably, and matingly cooperates with the curved upwardly facing surface 427 of the elongated male pin member 423 which was earlier described. The curved dove tailed shaped slot 450 has individual flange members 452 which extend towards one another, and which respectively cause the curved dove tailed slot 450 to assume a T-shaped configuration. However, it will be recognized that other shapes can work with equal success. Still further, it should be understood that the structure disclosed herein, that being, the curved elongated male pin member 423 and the curved dove tailed slot 450 may be exchanged, or otherwise substituted, one for the other, and the invention will operate with the same degree of success. The main body 443 of the arch wire insert 440 further defines an arch wire slot 460. The arch wire slot has opposite first and second ends 461 and 462, respectfully. The arch wire slot 460 is further defined by a top surface 463, and a bottom surface 464. As was earlier described, the arch wire slot 460 has top and bottom surfaces 463 and 464, and which are disposed in predetermined, substantially parallel, spaced relation one relative to the other. The main body 443 of the arch wire insert further defines a rear surface 465 which connects the top and bottom surfaces together. As will be seen in FIG. 18, a pair of passageways 466 are formed through the rear surface 465, and further allow the arch wire slot 460 to communicate with the multiplicity of engagement regions 430 which are formed in the immovable bracket body 410. This feature will be discussed in greater detail, below. As will be seen from a study of FIG. 18, it will be recognized that the rear surface 465, in combination with the top and bottom surfaces 463 and 464 respectively define individual recessed regions 467 which are located near the first and second ends 441 and 442 of the arch wire insert 440. These recessed regions have a predetermined cross-sectional dimension which facilitates the receipt of a structure incorporated, and made a feature of, the bracket body insert which will be received within the arch wire slot 460, and which is discussed in greater in the paragraphs, which follow.

Figure 19A:
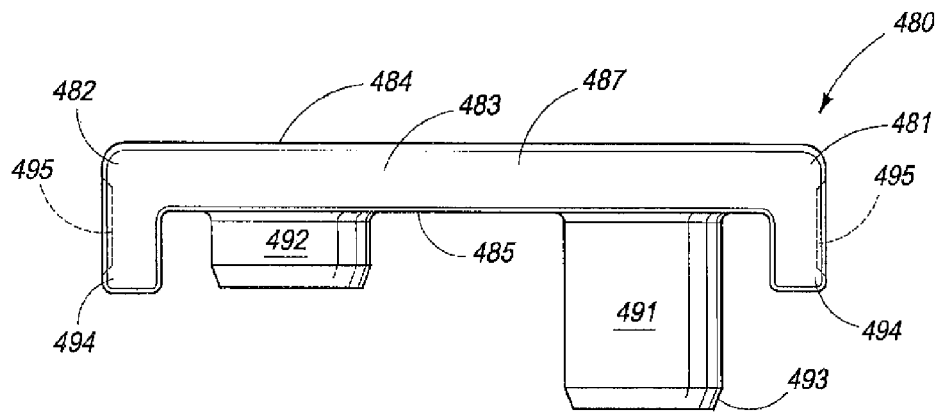
FIG. 19A illustrates side elevation view of one form of the bracket body insert which finds usefulness when used in the fourth form of the orthodontic bracket of the present invention.
Figure 19B:
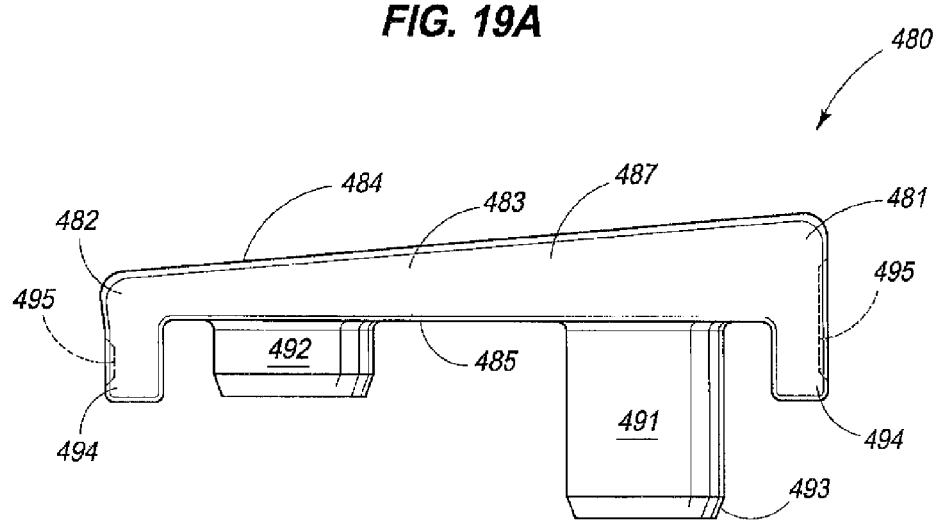
FIG. 19B illustrates a side elevation view of another form of the bracket body insert and which finds usefulness when used in the fourth form of the orthodontic bracket of the present invention.
Figure 19C:
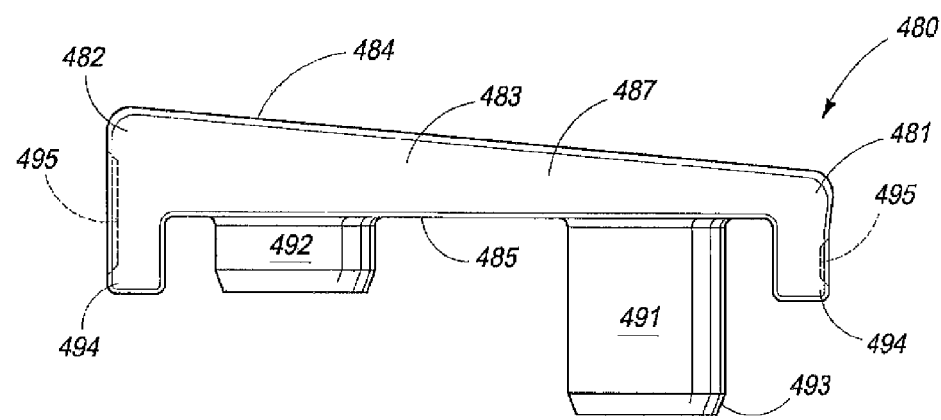
FIG. 19C illustrates a side elevation view of still another form of the bracket body insert and which finds usefulness when used in the fourth form of the orthodontic bracket of the present invention.

The fourth form of the invention 400 further includes a bracket body insert which is generally indicated by the numeral 480, and which is best understood by a study of FIGS. 19A, B and C, respectively. In this regard, the bracket body insert 480 has opposite first and second ends 481 and 482, respectively. The distance between the opposite first and second ends 481 and 482 is substantially equal to, or less than the distance as measured between the opposite ends 441 and 442 of the arch wire insert 440. As will be recognized, the bracket body insert 480, as depicted, typically does not extend beyond the first and second sides 413 and 414 of the immovable bracket body 410. However, it will be recognized that the bracket body insert 480 may be made longer so as to extend outwardly relative to the opposite sides of the immovable bracket body 410 in order to facilitate the use of the bracket body by being easier to see, or grasp by the clinician as the bracket body insert 480 is inserted or withdrawn from the arch wire slot 460. The bracket body insert 480 includes a main body 483 which has an anterior facing surface 484, and which forms a rear wall that defines, in part, the arch wire slot 460. Still further, the main body 483 has an opposite, posterior facing surface 485 which lies in rested, juxtaposed relation, thereagainst, the rear surface 465 as defined by the arch wire insert 440. The bracket body insert further defines top and bottom surfaces 486 and 487, respectively. The top and bottom surfaces are disposed in substantially parallel, spaced relation, one relative to the other. The distance between the top and bottom surfaces 486 and 487, respectively, is less than about the distance as defined between the top and bottom surfaces 463 and 464, and which define, in part, the arch wire slot 460. Therefore, it will be recognized that that bracket body insert 480 may be received within the arch wire slot 460 and further cooperates with same. As was the case with the other forms of the invention, the bracket body insert 480 includes a first, elongated, and longer dimensioned engagement member 491 which extends normally downwardly from a location near the first end 481. Still further, the bracket body insert 480 includes a second, and smaller engagement member 492 which extends from a location near the second end 482. The first and second engagement members 491 and 492, respectively, have a predetermined shape such that they may be matingly received and pass through the respective passageways 466 which are formed in the rear surface 465 of the arch wire insert 440, as was earlier described. The first and the longer of the engagement members 491, has a distal end 493 which is operable to be received within one of the multiplicity of engagement regions 430 which are formed in the immovable bracket body 410. Similar to that which was discussed with the other forms of the invention, the receipt of the distal end 493 in one of the multiplicity of engagement regions 430 is effective in fixedly, adjustably positioning the arch wire insert 440 in a given predetermined rotational orientation relative to the immovable bracket body 410 to achieve the benefits of the present invention. As will be seen by comparing the views of FIGS. 19A, 19B and 19C, respectively, the main body 483 may have a variable thickness dimension as measured between the anterior facing surface 484, and the posterior facing surface 485. As noted above, the anterior facing surface 484 forms a part of the arch wire slot 460. Because of the variable thickness dimension as provided by the arch wire insert 440, the arch wire insert 440 is able to variably adjust the cross-sectional dimension of the arch wire slot 460 which is defined between the surfaces 463, 464 and the anterior facing surface 484 of the bracket body insert 440 which forms the rear wall of the arch wire slot 460. As seen in FIGS. 19A, 19B and 19C, respectively, the bracket body insert 480 further includes movement restraining members 494 which extend normally downwardly from the opposite first and second ends 481 and 482. These movement restraining members are sized so as to be appropriately matingly received within the recessed regions 467 which are positioned endwardly of the arch wire slot 460 as earlier disclosed. Still further, as seen in FIGS. 19A, 19B and 19C respectively, a cavity 495 is formed in the movement restraining members 494, and which facilitate the gripping of the bracket body insert 480 by the clinician, or by the use of a tool employed by the clinician, in order to remove or place the bracket body insert 480, in an appropriate orientation within the arch wire slot 460.

Fifth Form of the Invention

The fifth form of the invention is best understood by FIGS. 20A, B, C and D, respectfully. In the fifth form of the invention it will be understood that the invention relates to a variation in the bracket body insert 500 which may be employed and utilized in the various forms of the invention discussed in this application. In this regard, it will be understood that the bracket body insert 500 as seen in FIGS. 20A, B, C and D, respectively, can be received in the previously described arch wire slots, of the several forms of the invention previously described. Again, the bracket body insert 500 may be utilized, on the one hand, to fix a selectively rotatably moveable bracket body as seen in the first form of the invention 20, or further it may be employed to selectively rotatably fix an arch wire insert as seen in the fourth form of the invention 400. Again, the bracket body insert 500 is received within an arch wire slot as defined by a bracket body as employed on the orthodontic bracket 10. Again, the bracket body insert 500 has first and second ends 501 and 502, respectively, and a main body 503, which has a height dimension which allows it to be readily received within the arch wire slot. Again, the length of the bracket body insert as measured between the first and second ends may be the same length as the arch wire slot, or may further extend outwardly therefrom so as to provide a convenient means for grasping the bracket body insert 500 by the clinician as the bracket body insert is placed into, or removed from the arch wire slot. The bracket body insert has an anterior facing surface 504 which forms a portion of the corresponding arch wire slot. Again, the thickness dimension of the main body 503 can either be uniform, or non-uniform depending upon the clinical situation being addressed on a patient's tooth 11. Again, the main body 503 has a posterior facing surface 505 which is located within the moveable or immovable bracket body depending upon the form of the invention being employed. The main body also has top and bottom surfaces 506 and 507, respectively. Again, the distance as measured between the top and bottom surfaces is less than about the distance as measured between the top and bottom surfaces which define, in part, the arch wire slot into which the bracket body insert 480 is being placed. In the fifth form of the invention 500, a pair of rigid planar surfaces 510 extend substantially normally outwardly relative to the anterior facing surface 504, and in a substantially coplanar orientation relative to the top and bottom surfaces 506 and 507, respectively of the main body 503. The pair of planar surfaces 510 include first and second planar surfaces 511 and 512, respectively. The first and second planar surfaces are substantially parallel to each other, and are further attached to the main body 503 at a weakened joint which is generally indicated by the numeral dotted line 513. The first and second planar surfaces define a reduced dimensioned predetermined cross-sectional region 514. This region 514 would, of course, be oriented within the existing arch wire slot as defined either by the bracket body, or the arch wire insert depending on the form of the invention as shown. However, this reduced dimension cross-sectional region 514 provides a clinician with yet another way of using smaller dimensioned arch wires in order to finely adjust the position of a patient's teeth 11 in order to provide a completed orthodontic treatment which puts all teeth of the patient in an appropriate orientation.

The first and second planar surfaces, as illustrated in FIGS. 20B and 20C, respectively, can be individually removed by the application of force which is applied to the individual planar surfaces 511 and 512, respectively. This is accomplished by breaking the first or second planar surfaces away at the weakened joint 513. In this manner, the clinician can adjust the relative orientation of the predetermined cross-sectional region 514 in the arch wire slot which receives the arch wire. This feature provides a multitude of treatment options and allows a clinician to use variously sized and dimensioned arch wires to finely adjust the final position of an individual patient's teeth 11 in a manner not possible, heretofore. The main body 503 further includes a first and longer engagement member 521 which extends from a position at or near the first end 501. Still further, and as earlier discussed the main body 503 has a second, shorter engagement member 522 which extends from a position near the second end 502. Again, the first, and longer engagement member has a distal end 523 which is operable to be received in one of the earlier described engagement regions formed in the bracket base, or in the bracket body depending upon the form of the invention in which the bracket body insert 500 is employed. Again, this same bracket body insert 500 has opposite movement restraining members 524 which are mounted on the opposite first and second ends 501 and 502, respectively. The movement restraining members 524 each have a cavity 525 which is formed therein, and which further gives a clinician an opportunity to easily grasp or otherwise engage the bracket body insert 500 to easily place it, or remove it, from the arch wire slot of the bracket body upon which it is employed.

In its broadest aspect therefore, the present invention includes an orthodontic bracket 400 which includes a bracket base 401 which is releasably affixed to an anterior facing surface 12 of a patient's tooth 11, and a bracket body 410 is mounted on the bracket base 401, and which further has an anterior facing surface 411 which defines a transversely disposed, and substantially cylindrically shaped cavity 420. In the invention as disclosed, an arch wire insert 440 having a main body 443 is defined, in part, by a longitudinal axis 444, and which is further received within the transversely disposed and substantially cylindrically shaped cavity 420. The main body 443 of the arch wire insert 440 further defines, at least in part, a transversely disposed arch wire slot 460 having a selectively adjustable cross-sectional dimension. The arch wire insert 460 is selectively rotatable about the longitudinal axis 444 thereof. In one form of the invention, as disclosed, a bracket body insert 480 is provided, and which is releasably received within the transversely disposed arch wire slot 460, and which further has a main body 483 which forms, at least in part, a portion of the arch wire slot 460. The bracket body insert 480 substantially releasably fixes the rotatable orientation of the arch wire slot 480 relative to the bracket body 410, and further selectively adjusts the cross-sectional dimension of the transversely disposed arch wire slot 460 while the bracket base 401 is releasably attached to the anterior facing surface 12 of the patient's tooth 11. In one form of the invention as disclosed, an arch wire 435 is received within the transversely disposed arch wire slot 460 and which, acting in combination with the arch wire insert 440 provides a multiplicity of selective torque expressions which individually forcibly act upon the patient's tooth 11. These individual torque expressions achieve predetermined first, second and third orders of movement 13, 14 and 15, respectively of the patient's tooth 11.

Sixth Form of the Invention

The sixth form of the invention is generally indicated in FIGS. 21 through 24, respectively. The sixth form of the invention 600 includes a bracket base which is generally indicated by the numeral 601. The bracket base, which is quite similar to that which was earlier disclosed with the other forms of the invention, includes a pad 602, which is defined by a peripheral edge 603. The pad 602 has an anterior facing surface 604, and an opposite, posterior facing surface 605. A coupling portion 610 is made integral with the anterior facing surface 604. The coupling portion 610 defines a curved, dove tail shaped slot, which is indicated by the numeral 611. The coupling portion 610 is similar to that which was earlier described with respect to the first form of the invention 20. The curved dove tail slot 611 is further defined by a pair of spaced, and angled sidewall 612, as illustrated in the drawings, and which forms a resulting truncated shaped passageway or channel, which is operable to receive a feature of the invention, which is made integral with the bracket body, as will be described below. The respective sidewalls 612 define, in part, an elevated, central region 613 of the coupling portion 610. The elevated central region 613 has a curved upwardly facing surface 614, having a curvature similar to the posterior facing surface of the bracket body, as will be described in the paragraph, below. Additionally, as will be seen in the drawings, a pair of curved guide channels 615 are formed on opposite sides of the curved dove tail shaped slot 611 and are operable to matingly couple with similar individual, curve-shaped rib structures which are formed in the posterior facing surface of the bracket body as described in the paragraph, below. As was described in the other forms of the invention, a multiplicity of engagement regions 616, are formed in the coupling portion 610, and are operable to be engaged by the distal end of a bracket body insert, as will also be described, below.

Figure 21:
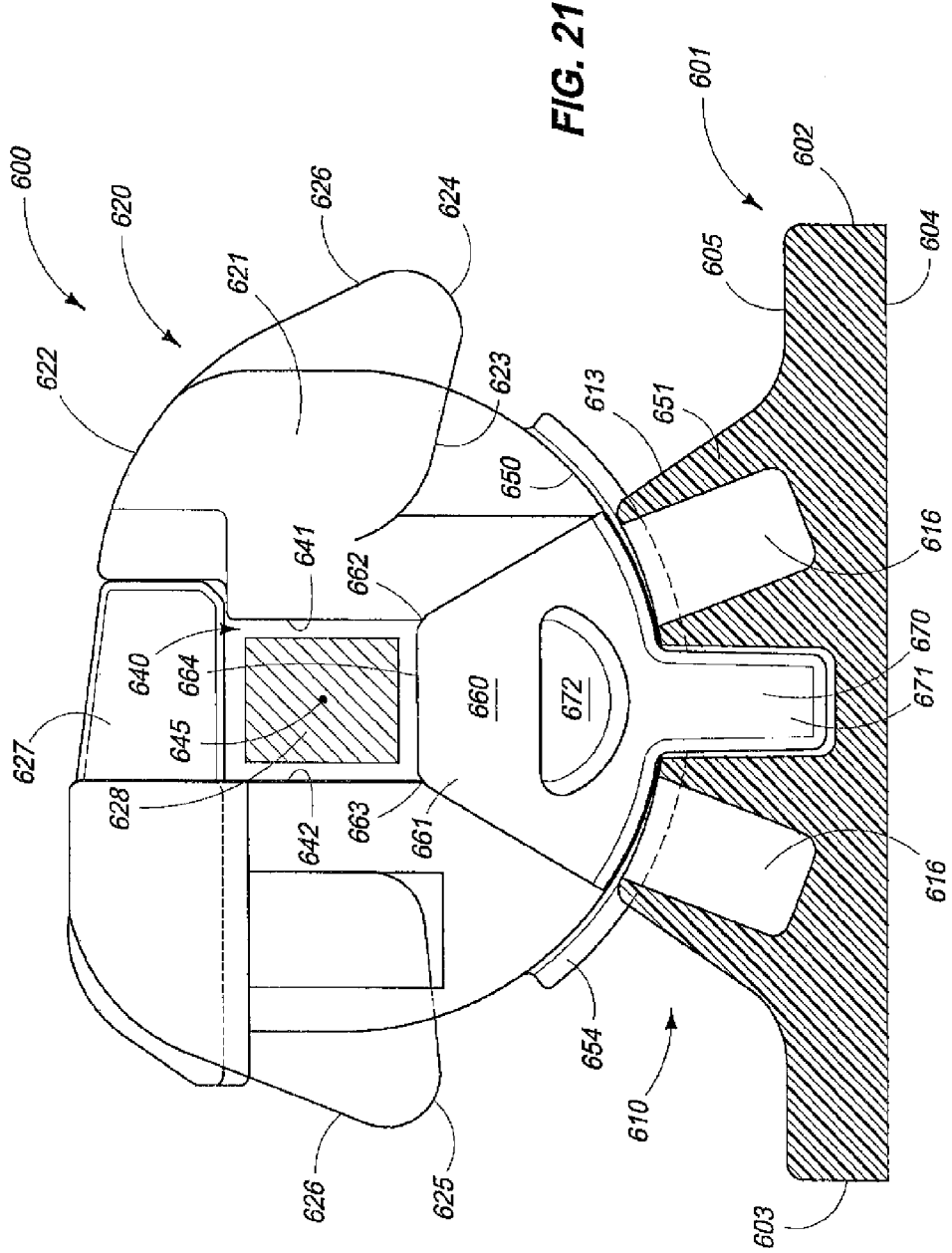
FIG. 21 is a mesial, side elevation view of yet another form of the orthodontic bracket of the present invention.
Figure 23:
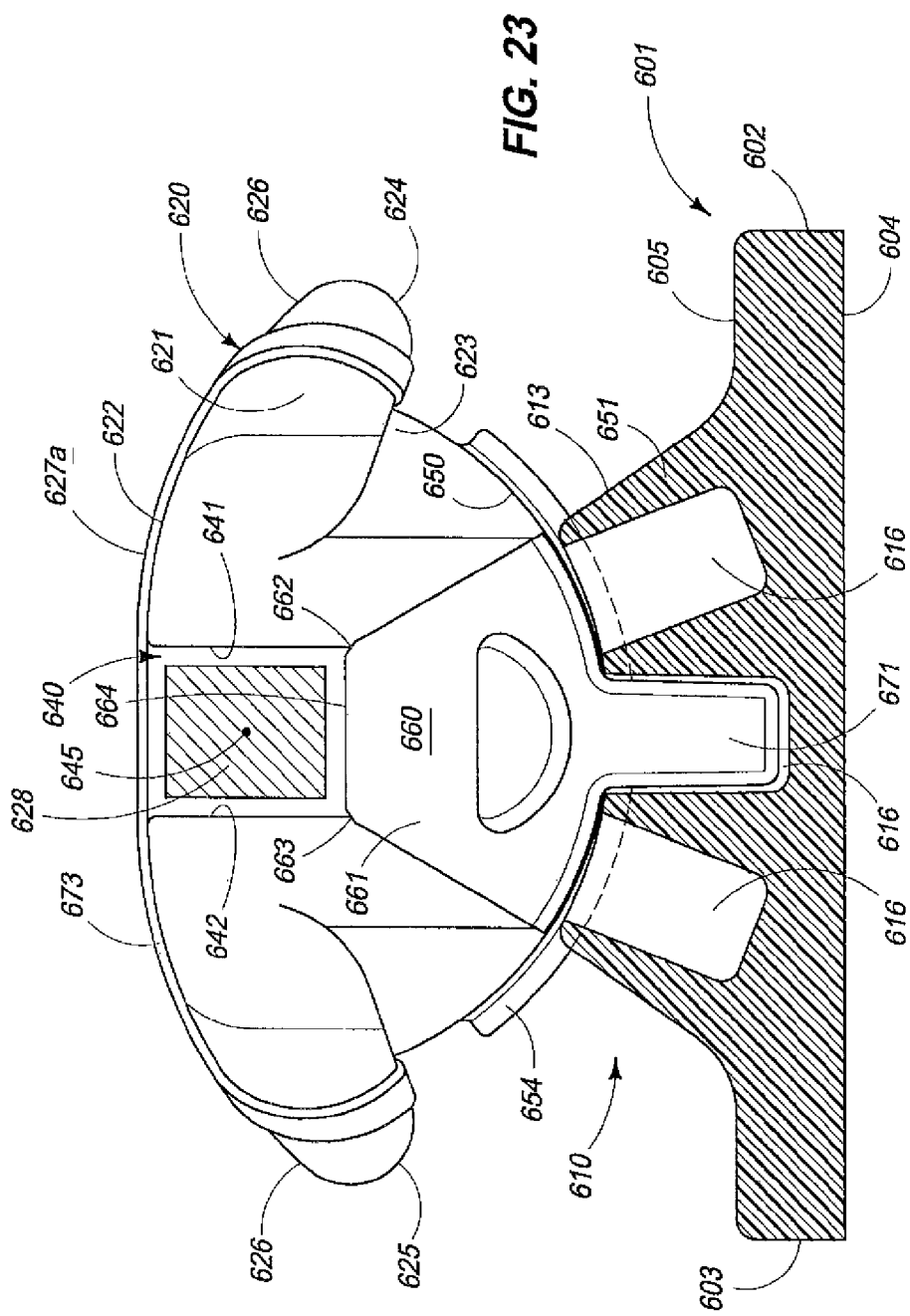
FIG. 23 is a greatly enlarged, side elevation view of still another form of the orthodontic bracket of the present invention.
Figure 24:
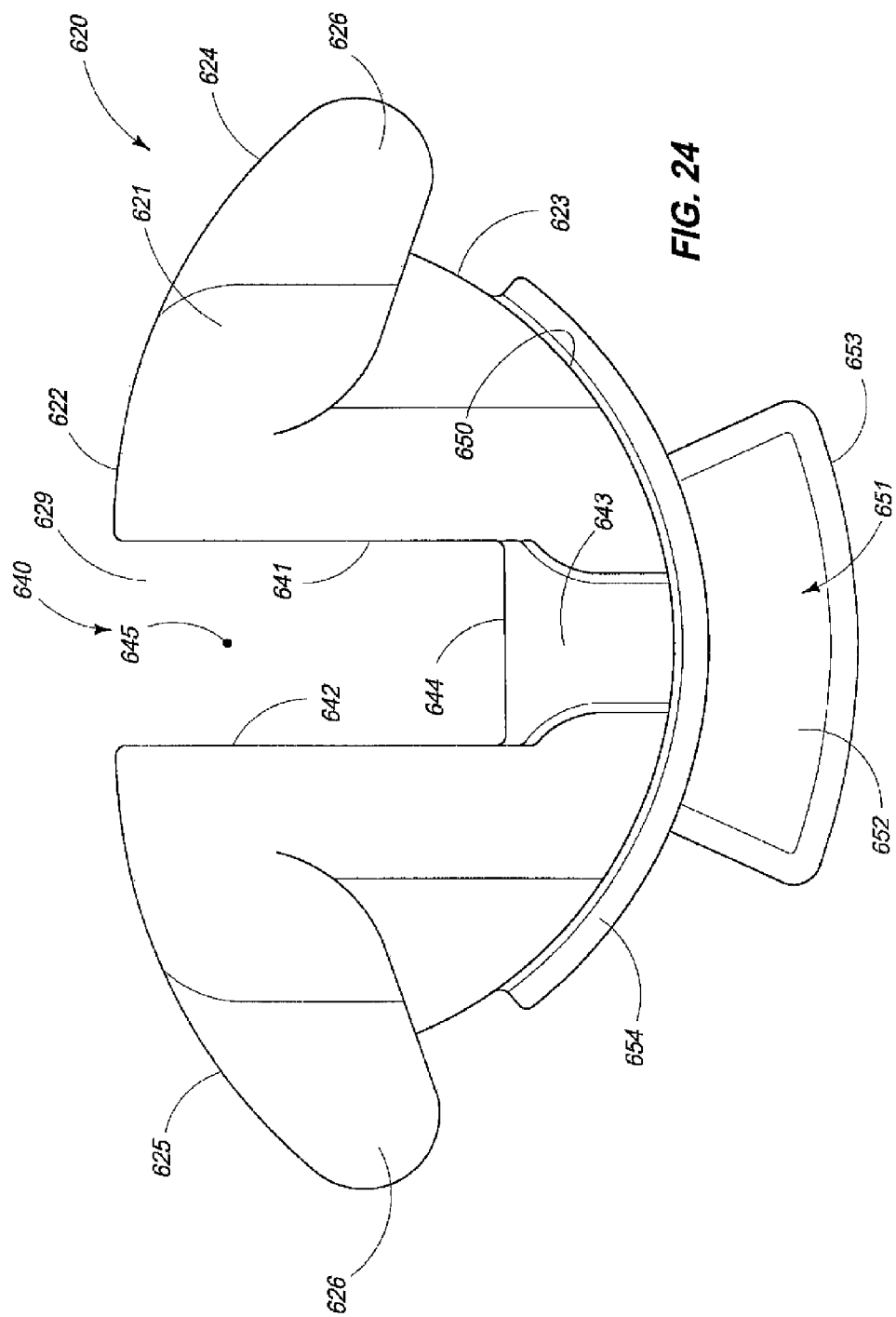
FIG. 24 is a side elevation view of a bracket body which forms a feature of one form of the present invention.

The sixth form of the invention 600 includes a bracket body 620, as seen in FIG. 21, and following. More specifically, the bracket body 620, as seen in the drawings, includes a main body 621, which has an anterior facing surface 622, and an opposite, posterior facing surface 623. In this regard the bracket body has a superior facing surface 624, and an opposite inferior facing surface 625. The superior and inferior facing surfaces 624 and 625, respectively, define individual tie wings which can be engaged by a ligature, and which may be utilized when employing the bracket body 620, which is illustrated in FIG. 23. With respect to the bracket body as illustrated in FIG. 21, it will be understood that the bracket body 620, as illustrated therein, is operable to cooperate with a movable gate 627, and whose operation is well known in the art. The bracket body 620, as seen in FIG. 23, represents a bracket body upon which a ligature of conventional design 627A can engage the aforementioned tie wings in order to secure the arch wire 628 therein. In this regard, the bracket body 620 defines an arch wire slot which is generally indicated by the numeral 640. The arch wire slot 640, similar to that earlier described, includes a top surface 641, and an opposite bottom surface 642. Still further as seen in FIG. 24, a pair of passageways 643 (only one of which is shown), is formed in the main body 621 of the bracket body 620 and which are individually located endwardly relative to the arch wire slot 640. The respective passageways 643 are operable to matingly cooperate with individual engagement members which are made integral with a bracket body insert, as will be described, below. As further seen in FIG. 23, the bracket body 620 defines a supporting wall 644, upon which a bracket body insert may rest in juxtaposed mating relation. The supporting wall 644 extends between the top and bottom surfaces 641 and 642, respectively.

Figure 22:
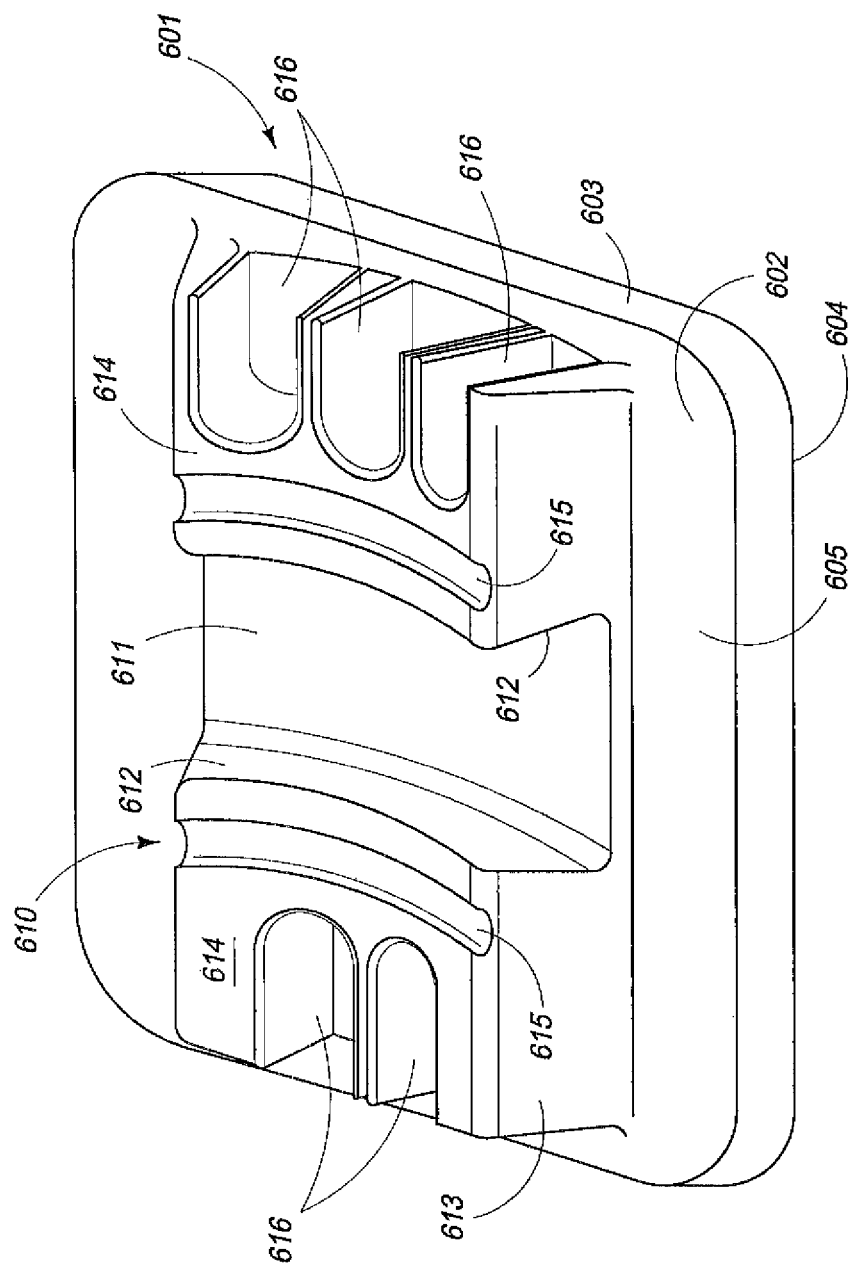
FIG. 22 is a greatly enlarged, perspective view of a bracket base and which finds usefulness in another form of the invention.

The sixth form of the invention 600, as seen in FIG. 21, and following, includes a complimentary, uniformly curved surface 650, which is made integral with the posterior facing surface 623. This complimentary, uniformly curved surface represents a male pin member 651, which is sized so as to matingly, and movably coupled with the coupling portion 610, and which is made integral with the bracket base 601. The male pin member 651 is defined, in part, by sidewall 652, which have an inclination similar to that of the respective sidewalls 612, which form a portion of the curved dove tail shaped slot 611. As seen in FIG. 22, it should be understood that the male pin member 651 has a somewhat truncated shape when viewed in cross-section, and which is dimensioned to be matingly received within the curved, dove-tail shaped slot 611, which forms a part of the coupling portion 610. Again, the male pin member 651 includes a complimentary curved surface 653 (FIG. 24), having a curvature similar to the curved dove-tail shaped slot 611. Still further, and as seen in FIG. 22, and adjacent to, and on the opposite sides of the male pin member 651, are a pair of elongated, and curved guide members 654, which are dimensioned to be received within the pair of curved guide channels 615, as seen in FIG. 22. The respective elongated guide member 654 are individually operable to guide or otherwise direct the bracket body 620 along a curved path of travel as it rotates within the coupling portion 610. As will be appreciated, and while the curved dove-tail shaped slot 611 is shown having a concave-like shape, and the male pin member 651, and more specifically the complimentary curved surface 653, is shown as being convexly shaped, it will be recognized that these respective shapes could be reversed, and positioned on the opposite structure, and thus achieve the same benefits as provided for in the present invention.

As illustrated in FIGS. 21 and 23, respectively, the sixth form of the invention 600 works, in combination, with a bracket body insert, and which is generally indicated by the numeral 660. The bracket body insert is similar in structure to that seen in FIG. 6. The bracket body insert has a main body 661, which is dimensioned to be received within an arch wire slot 640. Again, the main body has a top or superior facing surface 662, and an opposite, bottom facing surface 663. The main body 661 is received, and is positioned between, the top and bottom surfaces 641 and 642 of the arch wire slot 640. The bracket body insert 660 includes an anterior facing surface 664, which forms the rear wall of the arch wire slot 640, and which further extends between the top and bottom surfaces 641 and 642. Still further, the bracket body insert has a posterior facing surface (not shown) and which rests in juxtaposed relation thereagainst the supporting wall 644. Again, the thickness dimension as measured between the anterior facing surface 664, and posterior facing surface can be varied so as to allow the bracket body insert 660 to define an adjustable arch wire slot 640, which has a variable, pre-determined cross-sectional dimension which allows a clinician to apply varying amounts of torque to the arch wire 628, and which is positioned within the arch wire slot 640. Again, the bracket body insert 660 includes a pair of elongated engagement members 670, only one of which is shown (FIG. 21). One of the elongated engagement member 670, includes a distal end 671, which is operable to be received in one of the multiplicity of engagement regions 616. Again, the distal end 671 is operable to releasably, rotatably fix the orientation of the bracket body 620, in a given orientation relative to the bracket base 601. To adjust the sixth form of the invention 600, the bracket body insert 660 may be grasped at the respective recessed regions 672, which is formed in the main body 661, and moved anteriorly, outwardly relative to the arch wire slot 640. Thereafter, the bracket body 620 may be adjusted, appropriately, and then the bracket body insert 660, and more specifically the elongated engagement member 670, may be received in one of the multiplicity of engagement regions 616. Thereafter, the arch wire 628 may be placed back in the arch wire slot 640 and either the gate 627 closed, or in the alternative, the arch wire 628 may be secured in the arch wire slot 640, by means of a suitable ligature 627A, as seen in FIG. 23. The ligature as illustrated is not drawn to an appropriate size so as to allow an illustration of the inventive concepts.

The advantages of the sixth form of the invention should be readily apparent to those skilled in the art. With regard to the form of the invention, as seen in FIG. 21 and following, it will be recognized that the same bracket base 601, including the coupling portion 610, may be utilized for either, on the one hand, a self-ligating bracket arrangement, as seen in FIG. 21, or further an active self ligation bracket arrangement, as seen in FIG. 23. The sixth form of the invention 600 further allows the same bracket body insert 660 to be employed to affect either the use of the bracket body with a passive self-ligating arrangement (FIG. 21), or an active self-ligating arrangement (FIG. 23), or a conventional tied bracket. This particular form of the invention is quite desirable from a manufacturing standpoint inasmuch as the cost of manufacturing is substantially reduced and provides a range of passive and active self-ligating brackets, which may be useful in a wide range of clinical settings in a manner not possible, heretofore.

Operation

In its broadest aspect, the present invention relates to an orthodontic bracket, which is generally indicated by the numeral 10, and which includes a bracket base 21, which is releasably affixed to an anterior facing surface 12 of a patient's tooth 11. The orthodontic bracket 10 further includes a bracket body 40, which is borne on the bracket base 21, and which has an anterior facing surface 42, which defines a transversely disposed arch wire slot 60. The arch wire slot 60 further has opposite, first and second ends 61 and 62, respectively. The arch wire slot 60 has a selectively adjustable cross-sectional dimension, and further includes a central region or portion which is generally indicated by the numeral 66. As illustrated in the drawings, the arch wire slot 60 is moveable in both the vertical and horizontal planes, and has a central region, as earlier described. Still further, the arch wire slot 60 as noted above, has a selectively adjustable cross-sectional dimension. Further, the orthodontic bracket 10 includes an arch wire 90, which is received within the transversely disposed arch wire slot 60. The bracket body 40, acting in combination with the arch wire 90, is selectively adjustable so as to provide a multiplicity of selective torque expressions 13, 14 and 15, respectively, and which individually, forcibly act on the patient's tooth 11. These first, second and third orders of movement of the patient's tooth occur without a clinically predetermined manipulation of the arch wire 90, which is received in the transversely disposed arch wire slot 60. Further, rotation of the arch wire slot 60 in either of the vertical or horizontal planes is maintained about the central region 66 of the arch wire slot 60. This is a significant advancement in the way in which a clinician can address orthodontic maladies inasmuch as the fine adjustment of a tooth position can now be performed in a manner which substantially prevents any adverse vertical movement component or force vector being unduly applied to the patient's tooth 11.

More specifically, the present invention relates to an orthodontic bracket which is generally indicated by the numeral 600, and which is seen in FIG. 21, and following. The orthodontic bracket 600 includes a bracket base 601, having a pad 602, which is releasably affixed to an anterior facing surface 12 of a patient's tooth 11. The bracket base 601, as illustrated, has an anterior facing surface 604, which defines a coupling portion 610. The coupling portion further has a curved, anterior or upwardly facing surface 614. As seen in the drawings, a multiplicity of engagement regions 616 are formed in a predetermined spatial pattern in the curved anterior facing surface 614 of the coupling portion 610. As further illustrated in the drawings, a bracket body 620 is provided and which matingly, and moveably cooperates with the bracket base 601, and which further has an anterior facing surface 622 which defines an aperture which communicates with an arch wire slot 640. The arch wire slot 640 has spaced, top and bottom surfaces 641 and 642, respectively, and a given cross-sectional dimension. The transversely disposed arch wire slot 640 communicates with the aperture 629 which is defined by the anterior facing surface 622 of the bracket body 620. Still further, the transversely disposed arch wire slot 640 is further accessible from the anterior facing surface 622 of the bracket body 620. The bracket body 620 has a complimentary, curved, posterior facing surface 650, which matingly and moveably engages the curved anterior facing surface 614 of the coupling portion 610 of the bracket base 601. The present invention also includes a bracket body insert 660, which is releasably received within the transversely disposed arch wire slot 640, and which further has a main body 661, which forms a back wall 664 of the transversely disposed arch wire slot 640. The back wall 664 extends between the top and bottom surfaces 641 and 642, respectively, of the arch wire slot 640. The bracket body insert 660 further has a main body 661, which has a predetermined length, height and thickness dimension. The bracket body insert 660 selectively adjusts the cross-sectional dimension of the transversely disposed arch wire slot 640. The bracket body insert 660 further includes an elongated engagement member 670, which is oriented substantially perpendicularly relative to the main body 661 thereof, and which further has a distal end 671, which is operable to be received in one of the engagement regions 616 that are formed in the bracket base 601. The engagement member 670 of the bracket body insert 660 is effective in selectively fixing the rotatable orientation of the moveable bracket body 620 relative to the bracket base 601. The orthodontic bracket 600 further includes an arch wire 628, which is received within the transversely disposed arch wire slot 640. The moveable bracket body 640, acting in combination with the bracket body insert 660, selectively provides first, second and third order torque couples 13, 14 and 15, respectively, to a patient's tooth 11, to achieve a clinically desired positional correction of the patient's tooth 11, without the replacement of the orthodontic bracket base and/or the arch wire 628 during a predetermined clinical treatment regimen. Still further, the orthodontic bracket 600, in one form, and as seen in FIG. 21, further includes a moveable gate, which is positioned on the anterior facing surface 622, of the bracket body 620, and which further selectively occludes the aperture 629, which is defined by the anterior facing surface 622 of the bracket body 620. As seen in FIG. 23, and in an alternative possible variation or form of the invention, an active self-ligating bracket is shown, and which does not include such a gate assembly. As will be recognized from the drawings, the transversely disposed arch wire slot 640 is moveable in both the vertical and horizontal planes and has a central region 645. As will be recognized, and as was discussed earlier, during rotation of the arch wire slot 640, in either the vertical nor horizontal planes, the arch wire slot is substantially vertically maintained about the central region of the arch wire slot 645, thereby providing numerous benefits to the clinician which have not been available in other prior orthodontic assemblies which have been utilized heretofore. The orthodontic bracket 600, as seen, can achieve first, second and third orders of movement of the patient's tooth 11 without a clinically predetermined manipulation of the arch wire, and which is received in the transversely disposed arch wire slot. These features, in combination, are novel, and not found in a single prior art reference known to the inventors named in this patent application.

Therefore, it will be seen that the orthodontic bracket, in its various forms, as shown, in the present application, provides numerous means for readily, and easily treating a variety of orthodontic maladies in a manner not possible, heretofore. The present device is easy to employ; allows a clinician to use a single arch wire for the vast majority of clinical applications; allows a clinician to use lighter force arch wires, which provides greater comfort for patients; and additionally allows clinicians to rotate and move a patient's teeth in a manner which can achieve superior results, in shorter treatment times, and with greatly improved clinical results.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the Doctrine of Equivalents.

We claim:

1. An orthodontic bracket, comprising:
a bracket base which is releasably affixed to an anterior facing surface of a patient's tooth, and wherein a multiplicity of engagement regions are formed in a predetermined spatial pattern in the bracket base;
a bracket body borne on the bracket base, and which has an anterior facing surface which defines a transversely disposed arch wire slot having a given volume, and which further has opposite first and second ends, and wherein the transversely disposed arch wire slot is moveable in both a vertical and horizontal plane, and has a central region, and wherein the rotation of the bracket body to cause a subsequent rotation of the arch wire slot in either of the vertical or horizontal planes, is maintained about the central region of the arch wire slot;
a bracket body insert which is releasably received within the transversely disposed arch wire slot, and which further has a main body which occupies, at least in part, a portion of the volume of the arch wire slot, and wherein the bracket body insert has an engagement member having a distal end, and which is operable to be received within one of the multiplicity of engagement regions formed in the bracket base, and wherein the receipt of the distal end of the engagement member in one of the engagement regions releasably fixes the rotatable orientation of the bracket body relative to the bracket base; and
an arch wire received within the transversely disposed, arch wire slot, and wherein the bracket body, acting in combination with arch wire, is adjustable so as to provide a multiplicity of selective torque expressions which individually, and forcibly act upon the patient's tooth, and wherein the orthodontic bracket can be employed to achieve a first, second and third orders of movement of the patient's tooth without a clinically predetermined manipulation of the arch wire which is received in the transversely disposed, arch wire slot, and the bracket base may simultaneously remain affixed to the anterior facing surface of the patient's tooth for an entire orthodontic treatment period, and wherein the bracket body is partially, rotatably moveable relative to the bracket base and in a given axis of movement when the bracket base is mounted on the anterior facing surface of the patient's tooth, and wherein the bracket body can be releasably detached from the bracket base, and an alternative bracket body releasably reattached to the bracket base during the orthodontic treatment period.

2. a bracket base having a pad which is releasably affixed to an anterior facing surface of a patient's tooth, and wherein the bracket base has an anterior facing surface which defines a coupling portion having a curved anterior facing surface, and wherein a multiplicity of engagement regions are formed in a predetermined spatial pattern in the curved anterior facing surface of the coupling portion; a bracket body which matingly, and moveably cooperates with the bracket base, and which has an anterior facing surface defining an aperture, and which further defines, in part, an arch wire slot having a given volume, and which is further defined by spaced, top and bottom surfaces, and a given cross-sectional dimension, and wherein the transversely disposed arch wire slot communicates with the aperture which is defined by the anterior facing surface of the bracket body, and is further accessible from the anterior facing surface of the bracket body, and wherein the bracket body has a complementary, curved, posterior facing surface which matingly, and moveably engages the curved, anterior facing surface of the coupling portion of the bracket base; a bracket body insert which is releasably received within the transversely disposed arch wire slot, and which further has a main body which is juxtaposed relative to a back wall of the transversely disposed arch wire slot, and occupies, at least in part, a portion of the volume of the arch wire slot, and wherein the main body of the bracket body extends between the top and bottom surfaces of the arch wire slot, and wherein the main body of the bracket body insert has a predetermined length, height and thickness dimension, and wherein the bracket body insert, when received in the arch wire slot, selectively adjusts the cross-sectional dimension of the transversely disposed arch wire slot by occupying a portion of the volume of the arch wire slot, and wherein the bracket body insert further includes an engagement member which is oriented substantially perpendicularly relative to the main body thereof, and which further has a distal end which is operable to be received in one of the engagement regions formed in the bracket base, and wherein the engagement member of the bracket body insert is effective in selectively fixing the rotatable orientation of the moveable bracket body relative to the bracket base; and an arch wire received within the transversely disposed arch wire slot, and wherein the moveable bracket body, acting in combination with the bracket body insert, selectively provides first, second, and third order torque couples to a patient's tooth to achieve a clinically desired positional correction to the patient's tooth without the replacement of the orthodontic bracket base during the a predetermined clinical treatment regimen.

3. An orthodontic bracket as claimed in claim 2, and wherein the bracket body includes multiple bracket body forms which can be releasably detached from the bracket base; and wherein the bracket base remains affixed to the patient's tooth while the respective bracket body forms are releasably detached, and then reattached to the bracket base.

4. An orthodontic bracket as claimed in claim 3, and further comprising: a gate which is moveably borne by the anterior facing surface of the bracket body and which selectively occludes the aperture which is defined by the anterior facing surface of the bracket body.

5. An orthodontic bracket as claimed in claim 3, and wherein the transversely disposed arch wire slot is moveable in both the vertical and horizontal plane, and has a central region, and wherein rotation of the arch wire slot in either the vertical or horizontal plane is substantially maintained about the central region of the arch wire slot.

6. An orthodontic bracket, comprising:
a bracket base having a posterior facing surface which is affixed to a patient's tooth which is undergoing an orthodontic treatment, and an opposite anterior facing surface, and wherein a multiplicity of engagement regions are formed in the anterior facing surface of the bracket base;
a bracket body which releasably and moveably cooperates with the anterior facing surface of the bracket base in a given axis, and which further defines an arch wire slot that has a given volume;
a bracket body insert having a main body which is dimensioned so as be received in, and occupy a portion of the arch wire slot, and wherein the main body of the bracket body insert permits the resulting arch wire slot to have a selective cross-sectional dimension, and wherein the bracket body insert has an engagement member which has a distal end, and which is received within one of the multiplicity of engagement regions which are formed in the anterior facing surface of the bracket base, and wherein the engagement member fixes an orientation of the bracket body relative to the bracket base when the distal end is received in one of the engagement regions; and
an arch wire received within the arch wire slot, and which can be employed to impart first, second and third order movements to the patient's tooth.

* * * * *